(12) United States Patent
Nishide et al.

(10) Patent No.: US 7,522,695 B2
(45) Date of Patent: Apr. 21, 2009

(54) X-RAY CT APPARATUS

(75) Inventors: Akihiko Nishide, Tokyo (JP); Naoyuki Kawachi, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 11/489,065

(22) Filed: Jul. 19, 2006

(65) Prior Publication Data

US 2007/0019779 A1 Jan. 25, 2007

(30) Foreign Application Priority Data

Jul. 19, 2005 (JP) .............................. 2005-208235

(51) Int. Cl.
  *G21N 23/083* (2006.01)
  *H05G 1/38* (2006.01)
(52) U.S. Cl. ...................... 378/4; 378/98.8; 250/370.09
(58) Field of Classification Search ............... 378/4–20, 378/901, 62, 98.8, 114–116, 146–152, 156, 378/210; 250/370.09, 370.1, 370.11, 366, 250/367, 362, 363.1, 363.01, 363.02, 370.01, 250/370.08–9, 370.14

See application file for complete search history.

(56) References Cited

U.S. PATENT DOCUMENTS

| | | | | |
|---|---|---|---|---|
| 3,755,672 A * | 8/1973 | Edholm et al. | ............... | 378/158 |
| 4,200,799 A * | 4/1980 | Saito | ........................... | 378/13 |
| 4,638,499 A * | 1/1987 | Eberhard et al. | ............... | 378/7 |
| 5,033,075 A * | 7/1991 | DeMone et al. | ............ | 378/156 |
| 5,054,041 A * | 10/1991 | Hampel | ......................... | 378/4 |
| 5,185,775 A * | 2/1993 | Sirvin | ........................ | 378/156 |
| 5,237,599 A * | 8/1993 | Gunji et al. | ................. | 378/148 |
| 5,396,889 A * | 3/1995 | Ueda et al. | .................. | 600/407 |
| 5,974,109 A * | 10/1999 | Hsieh | ......................... | 378/19 |
| 6,023,494 A | 2/2000 | Senzig et al. | | |
| 6,115,448 A | 9/2000 | Hoffman | | |
| 6,157,696 A * | 12/2000 | Saito et al. | .................... | 378/19 |
| 6,198,791 B1 | 3/2001 | He et al. | | |
| 6,215,843 B1 * | 4/2001 | Saito et al. | .................... | 378/19 |
| 6,243,438 B1 * | 6/2001 | Nahaliel et al. | ............... | 378/19 |

(Continued)

FOREIGN PATENT DOCUMENTS

EP        0950372 A1    10/1999

(Continued)

OTHER PUBLICATIONS

European Search Report for application for EP 06253787, dated Dec. 17, 2007.

*Primary Examiner*—Anastasia Midkiff
(74) *Attorney, Agent, or Firm*—Armstrong Teasdale LLP

(57) ABSTRACT

A data acquisition device, which has an X-ray detector including a plurality of channel widths at which channels at its central portion are fine and channels at its peripheral portions are coarse or rough, and a plurality of data acquisition ranges including a data acquisition range wide in a channel direction and a data acquisition range narrow in the channel direction, and which is capable of performing switching among the data acquisition ranges for each data acquisition, is used to perform data acquisition on the channels fine at the central portion in the data acquisition range narrow in the channel direction, whereby an X-ray CT apparatus is provided which is capable of performing high-resolution imaging and brings about more satisfactory image quality.

16 Claims, 33 Drawing Sheets

U.S. PATENT DOCUMENTS

| | | |
|---|---|---|
| 6,275,562 B1 | 8/2001 | He et al. |
| 6,292,527 B1 * | 9/2001 | Guendel ..................... 378/15 |
| 6,385,278 B1 * | 5/2002 | Hsieh ........................... 378/8 |
| 6,400,793 B2 | 6/2002 | Doubrava et al. |
| 6,404,841 B1 | 6/2002 | Pforr et al. |
| 6,445,764 B2 | 9/2002 | Gohno et al. |
| 6,895,077 B2 * | 5/2005 | Karellas et al. ........... 378/98.3 |
| 2005/0053191 A1 * | 3/2005 | Gohno et al. ................. 378/19 |

FOREIGN PATENT DOCUMENTS

| | | |
|---|---|---|
| EP | 1502548 A1 | 2/2002 |
| EP | 1216662 A2 | 6/2002 |
| EP | 1498908 A2 | 1/2005 |
| JP | 2000-193750 | 7/2000 |
| WO | 9930616 | 6/1999 |
| WO | 9930616 A1 | 6/1999 |

* cited by examiner

24
Multi-Row X-Ray Detector

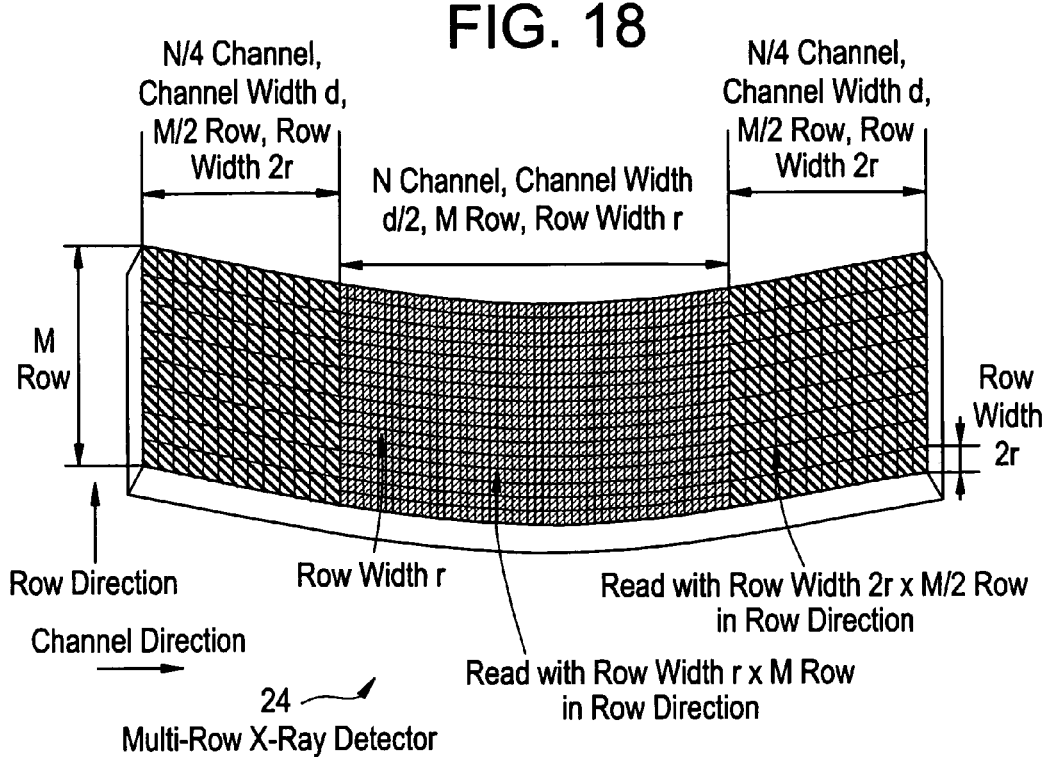
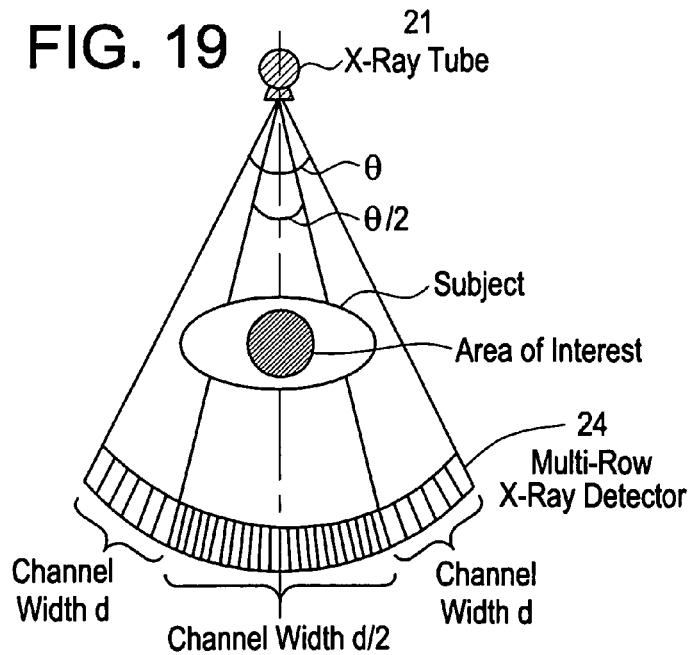

Area to be Imaged

Profile made to Elliptic Approximation

Predictable if Equivalent to Sir

Predictable if Equivalent to Sir

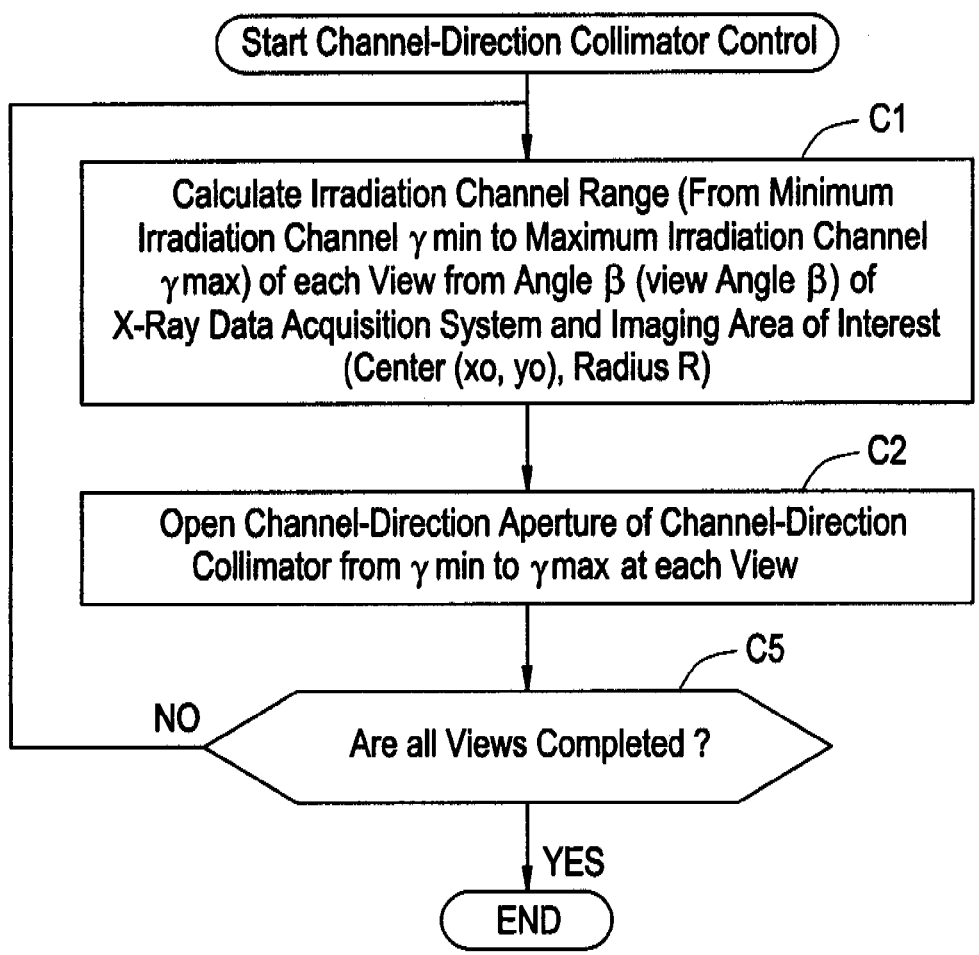

Kernel LR: Image reconstruction function for normal mode at detector channel pitch d
Kernel HR: Image reconstruction function for high resolution mode at Detector Channel pitch d/2

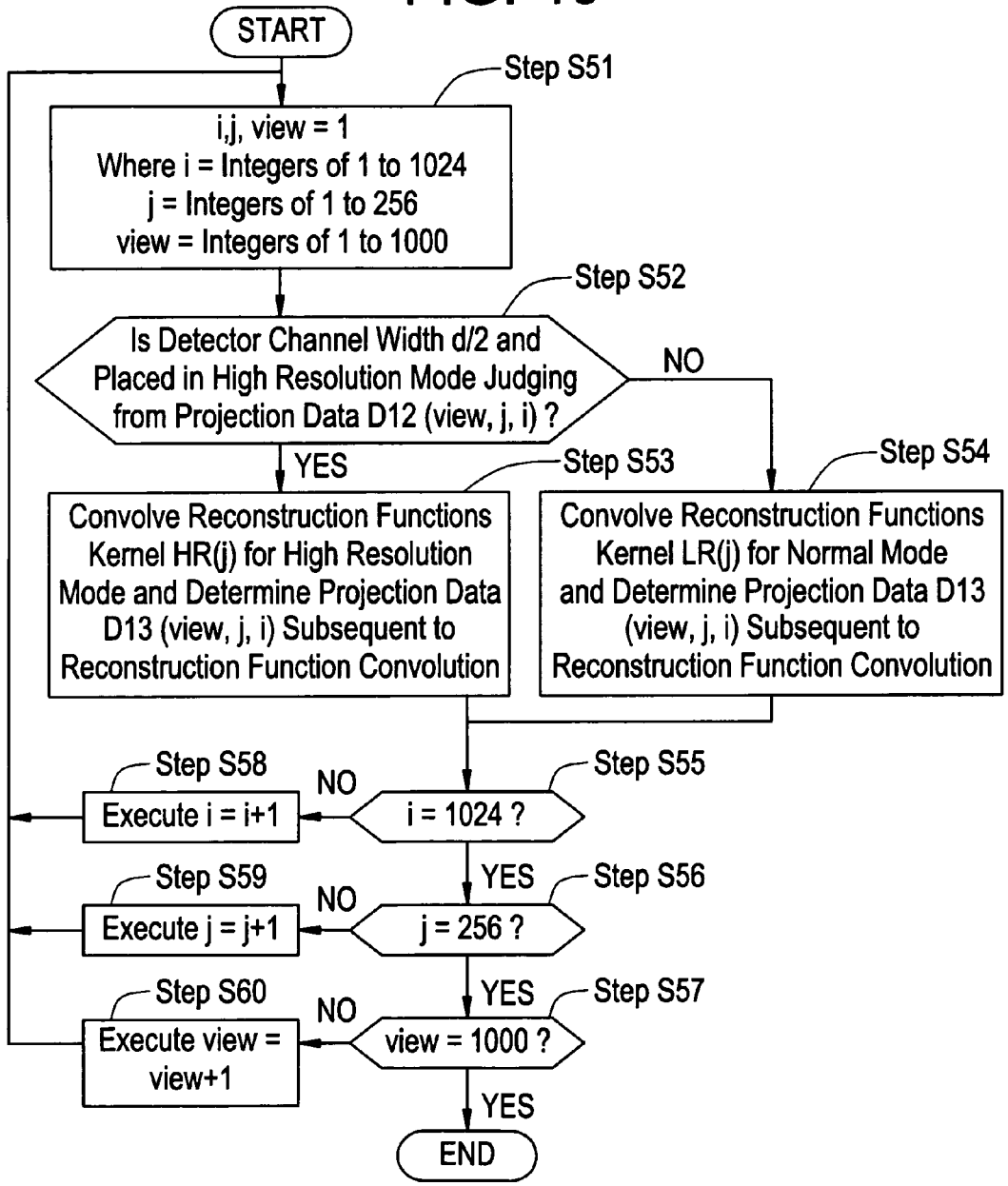

ly to the X-ray generator and the detector,
thereby acquiring projection data of the X rays transmitted
through a subject disposed between the X-ray generator and
the detector; image reconstructing means which image-re-
constructs the projection data acquired from the X-ray data
acquisition means; and display means which displays an
image-reconstructed image, wherein the X-ray data acquisi-
tion means has a plurality of data acquisition ranges
$1_1 \geq 1_2 \geq \ldots \geq 1_i \geq \ldots \geq 1_{n-1} \geq 1_n$ from the data acquisition
range $1_1$ wide in a channel direction of the detector to the data
acquisition range $1_n$ narrow in the channel direction, and is
configured in such a manner that the data acquisition ranges
are switchable every data acquisition.

X-RAY CT APPARATUS

CROSS REFERENCE TO RELATED APPLICATIONS

This application claims the benefit of Japanese Application No. 2005-208235 filed Jul. 19, 2005.

BACKGROUND OF THE INVENTION

An X-ray detector used in an X-ray CT apparatus, like a multi-row X-ray detector or a two-dimensional X-ray area detector of a matrix structure typified by a flat panel ahs heretofore been fabricated at constant intervals (pitches) and with a constant channel width as shown in FIG. 12 (refer to, for example, Japanese Unexamined Patent Publication No. 2000-193750).

An X-ray detector used in an X-ray CT apparatus, like a multi-row X-ray detector or a two-dimensional X-ray area detector of a matrix structure typified by a flat panel has heretofore been fabricated at constant intervals (pitches) and with a constant channel width as shown in FIG. 12 (refer to, for example, a patent document 1).

[Patent Document 1] Japanese Unexamined Patent Publication No. 2000-193750

Therefore, even if the imaging area is made small in an attempt to see it in high resolution, the tomographic image is merely blurred and hence a tomographic image of high resolution was not obtained. Although a slight improvement in contrast and an improvement in resolution are performed by slightly intensifying a high-frequency or RF region of a reconstruction function, an increase in noise and an increase in artifact have been brought about as adverse effects.

SUMMARY OF THE INVENTION

Therefore, an object of the present invention is to provide an X-ray CT apparatus capable of imaging or photographing a high-resolution X-ray tomographic image.

Another object of the present invention is to provide an X-ray CT apparatus capable of obtaining high resolution when a small imaging area is taken.

A further object of the present invention is to provide an X-ray CT apparatus which reduces the amount of used X rays and effectively uses the X rays thereby to enable a reduction in exposure of a subject to the X rays.

In a first aspect, the present invention provides an X-ray CT apparatus comprising X-ray data acquisition means which allows an X-ray generator, and a multi-row X-ray detector provided in opposing relationship to the X-ray generator and detecting X rays or a two-dimensional X-ray area detector of a matrix structure to be rotated about a center of rotation placed between the X-ray generator and the detector, thereby acquiring projection data of the X rays transmitted through a subject disposed between the X-ray generator and the detector; image reconstructing means which image-reconstructs the projection data acquired from the X-ray data acquisition means; and display means which displays an image-reconstructed image, wherein the X-ray data acquisition means is configured in such a manner that a detector channel width d2 at each peripheral portion of the detector as viewed in a channel direction becomes d1<d2 with respect to a detector channel width d1 at a central portion thereof as viewed in the channel direction, or a plurality of detector widths ($d_1$, $d_2, \ldots d_i, \ldots d_{n-1}, d_n$) provided from the central portion of the detector as viewed in the channel direction to the peripheral portion thereof satisfy $d_1 \leq d_2 \leq \ldots \leq d_i \leq \ldots \leq d_{n-1} \leq d_n$.

In the X-ray CT apparatus according to the first aspect, since X-ray detector channels narrower in channel width concentrate on the central portion, spatially high-resolution X-ray CT imaging can be conducted by performing data acquisition and image reconstruction using the X-ray detector channels narrow in channel width at the central portion.

In a second aspect, the present invention provides an X-ray CT apparatus comprising X-ray data acquisition means which allows an X-ray generator, and a multi-row X-ray detector provided in opposing relationship to the X-ray generator and detecting X rays or a two-dimensional X-ray area detector of a matrix structure to be rotated about a center of rotation placed between the X-ray generator and the detector, thereby acquiring projection data of the X rays transmitted through a subject disposed between the X-ray generator and the detector; image reconstructing means which image-reconstructs the projection data acquired from the X-ray data acquisition means; and display means which displays an image-reconstructed image, wherein the X-ray data acquisition means has a plurality of data acquisition ranges $1_1 \geq 1_2 \geq \ldots \geq 1_i \geq \ldots \geq 1_{n-1} \geq 1_n$ from the data acquisition range $1_1$ wide in a channel direction of the detector to the data acquisition range $1_n$ narrow in the channel direction, and is configured in such a manner that the data acquisition ranges are switchable every data acquisition.

In the X-ray CT apparatus according to the second aspect, since the narrower data acquisition range exists in the central portion, data acquisition is effected on the narrower data acquisition range of the central portion with fine channel widths and intervals and image reconstruction is performed, thereby enabling spatially high-resolution X-ray CT imaging.

In a third aspect, the present invention provides an X-ray CT apparatus wherein the X-ray data acquisition means performs data acquisition at a portion narrow in detector channel width, or the central portion of the detector as viewed in the channel direction when data acquisition is performed in the data acquisition range narrow as viewed in the channel direction of the detector.

In the X-ray CT apparatus according to the third aspect, since the detector channels narrower in channel width concentrate on the central portion and the narrower data acquisition range exists, data acquisition is effected on the narrower data acquisition range of the central portion with fine channel widths and at fine channel intervals and image reconstruction is performed, thereby enabling spatially high-resolution X-ray CT imaging.

In a fourth aspect, the present invention provides an X-ray CT apparatus wherein the X-ray data acquisition means has a plurality of channels at which data acquisition is performed.

In the X-ray CT apparatus according to the fourth aspect, since the number of the detector channels at which the data acquisition is performed, is switched in plural modes, data about a small number of detector channels at the central portion are acquired at high speed in a mode for a small number of channels and at the maximum value of a sampling rate of an A/D converter of the X-ray data acquisition means, and image reconstruction is performed, thereby enabling X-ray CT imaging high in resolution in terms of time.

In a fifth aspect, the present invention provides an X-ray CT apparatus wherein the X-ray data acquisition means has a plurality of channels at which data acquisition is performed, and a plurality of views.

In the X-ray CT apparatus according to the fifth aspect, since the number of the detector channels at which the data acquisition is performed, is switched in plural modes and the number of the views at which the data acquisition is performed, is switched in plural modes, data about a small number of detector channels at the central portion are acquired at high speed in the maximum value of a sampling rate of the A/D converter of the X-ray data acquisition means and in a mode for a small number of views, and image reconstruction is performed, thereby enabling X-ray CT imaging high in resolution in terms of time.

In a sixth aspect, the present invention provides an X-ray CT apparatus wherein the X-ray data acquisition means has a plurality of rows at which data acquisition is performed, and the number of the rows differs according to each channel position.

In the X-ray CT apparatus according to the sixth aspect, detector channels large in the number of rows as viewed in a z direction are concentrated on the central portion and in this condition, data acquisition is effected on the narrow data acquisition range of the central portion with fine channel widths and at fine channel intervals, and image reconstruction is performed, thereby enabling spatially high-resolution X-ray CT imaging.

In a seventh aspect, the present invention provides an X-ray CT apparatus wherein the X-ray data acquisition means has a plurality of data acquisition sampling periods at which data acquisition is performed.

In an eighth aspect, the present invention provides an X-ray CT apparatus wherein the X-ray data acquisition means has a plurality of data acquisition sampling periods at which data acquisition is performed, and the data acquisition sampling periods differ according to channel positions.

In the X-ray CT apparatus according to the seventh and eight aspects, data about a small number of detector channels at the central portion are collected or acquired at high speed in a mode short in data acquisition sampling period, and image reconstruction is carried out, whereby X-ray CT imaging high in resolution in terms of time is enabled.

In a ninth aspect, the present invention provides an X-ray CT apparatus including control means which controls an X-ray irradiation area in such a manner that X rays are radiated only into some of the range narrow in detector channel width, of the central portion of the detector as viewed in the channel direction or its inner range, the data acquisition range narrow in the channel direction of the detector or its inner range, or some of the data acquisition range narrow in the channel direction of the detector, i.e., the range narrow in detector channel width, of the central portion as viewed in the channel direction or its inner range.

In the X-ray CT apparatus according to the ninth aspect, since the irradiated X rays can be optimized narrower and radiated in the channel direction by the control means when data acquisition is done in the narrower data acquisition range of the central portion, subject's tomogram imaging at low exposure to radiation can be carried out.

In a tenth aspect, the present invention provides an X-ray CT apparatus having means which limits an X-ray irradiation area in such a manner that X rays are radiated into some range in the channel direction of the detector, which is fine in channel at the central portion as viewed in the channel direction of the detector or its inner range, the data acquisition range narrow in the channel direction of the detector or its inner range, or the data acquisition range narrow in the channel direction of the detector, i.e., the range for the fine channels of the central portion as viewed in the channel direction or its inner range.

In the X-ray CT apparatus according to the tenth aspect, since the irradiated X rays can be optimized narrower and radiated in the channel direction by the limiting means when data acquisition is performed in the narrower data acquisition range of the central portion, subject's tomogram imaging at low exposure to radiation can be performed.

The present invention can provide an X-ray CT apparatus capable of imaging or photographing a high-resolution X-ray tomographic image. Also, the present invention is capable of providing an X-ray CT apparatus capable of obtaining high resolution when a small imaging area is taken. Further, the present invention can provide an X-ray CT apparatus which reduces the amount of used X rays and effectively use the X rays to thereby enable a reduction in exposure of a subject to the X rays.

Further objects and advantages of the present invention will be apparent from the following description of the preferred embodiments of the invention as illustrated in the accompanying drawings.

BRIEF DESCRIPTION OF THE DRAWINGS

FIG. 18 is a diagram showing a row of modes for reading in row widths large in number and fine at an inner central portion of a multi-row X-ray detector having a plurality of types of channel widths and data acquisition ranges, and in row widths small in number and coarse at its outer peripheral portions.

FIG. 19 is a diagram illustrating the manner in which a subject is large and its area of interest is small.

FIG. 33 is a diagram showing feed forward control of the channel-direction collimator.

FIG. 40 is a flow diagram showing convolution of reconstruction functions where a plurality of types of X-ray detector channel widths exist.

DETAILED DESCRIPTION OF THE INVENTION

Figure 1:
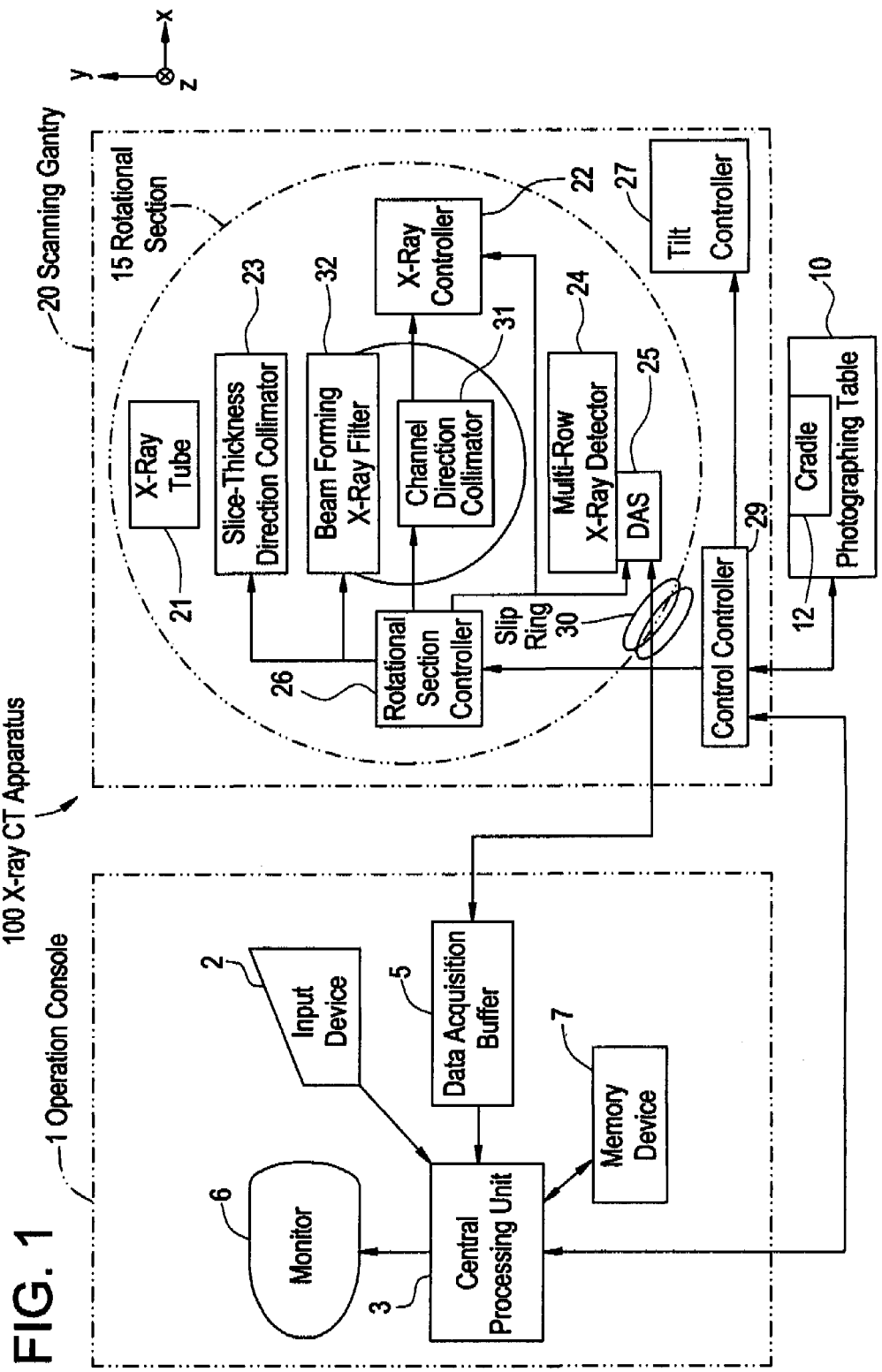
FIG. 1 is a block diagram showing an X-ray CT apparatus according to one embodiment of the present invention.

The present invention will hereinafter be described in further detail by embodiments illustrated in the drawings. Incidentally, the present invention is not limited thereby.

Embodiment 1

FIG. 1 is a configurational block diagram of an X-ray CT apparatus according to one embodiment of the present invention. The X-ray CT apparatus 100 is equipped with an operation console 1, a photographing or imaging table 10, and a scanning gantry 20.

The operation console 1 is equipped with an input device 2 which accepts an operator's input, a central processing unit 3 which executes an image reconstructing process or the like, a data acquisition buffer 5 which acquires or collects projection data acquired by the scanning gantry 20, a monitor 6 which displays a CT image reconstructed from the projection data, and a memory device 7 which stores programs, data and an X-ray CT image therein.

The photographing table 10 is equipped with a cradle 12 which places a subject thereon and which takes it in a cavity section of the scanning gantry 20 and takes it out therefrom. The cradle 12 is moved up and down by a motor built in the photographing table 10 and moved linearly along the photographing table 10. The direction in which the cradle 12 of the photographing table 10 moves is defined as a z direction.

The scanning gantry 20 is equipped with an X-ray tube 21, an X-ray controller 22, a slice-thickness direction collimator 23, a multi-row X-ray detector 24, a DAS (Data Acquisition System) 25, a rotational section controller 26 which controls the X-ray tube 21 or the like being rotated about a body axis of the subject, and a control controller 29 which swaps control signals or the like with the operation console 1 and the photographing table 10. The scanning gantry 20 can be tilted±about 30° or so forward and rearward as viewed in the z direction by a tilt controller 27. In addition to the above, the scanning gantry 20 has a channel-direction collimator 31 and a beam forming X-ray filter 32.

Figure 2:
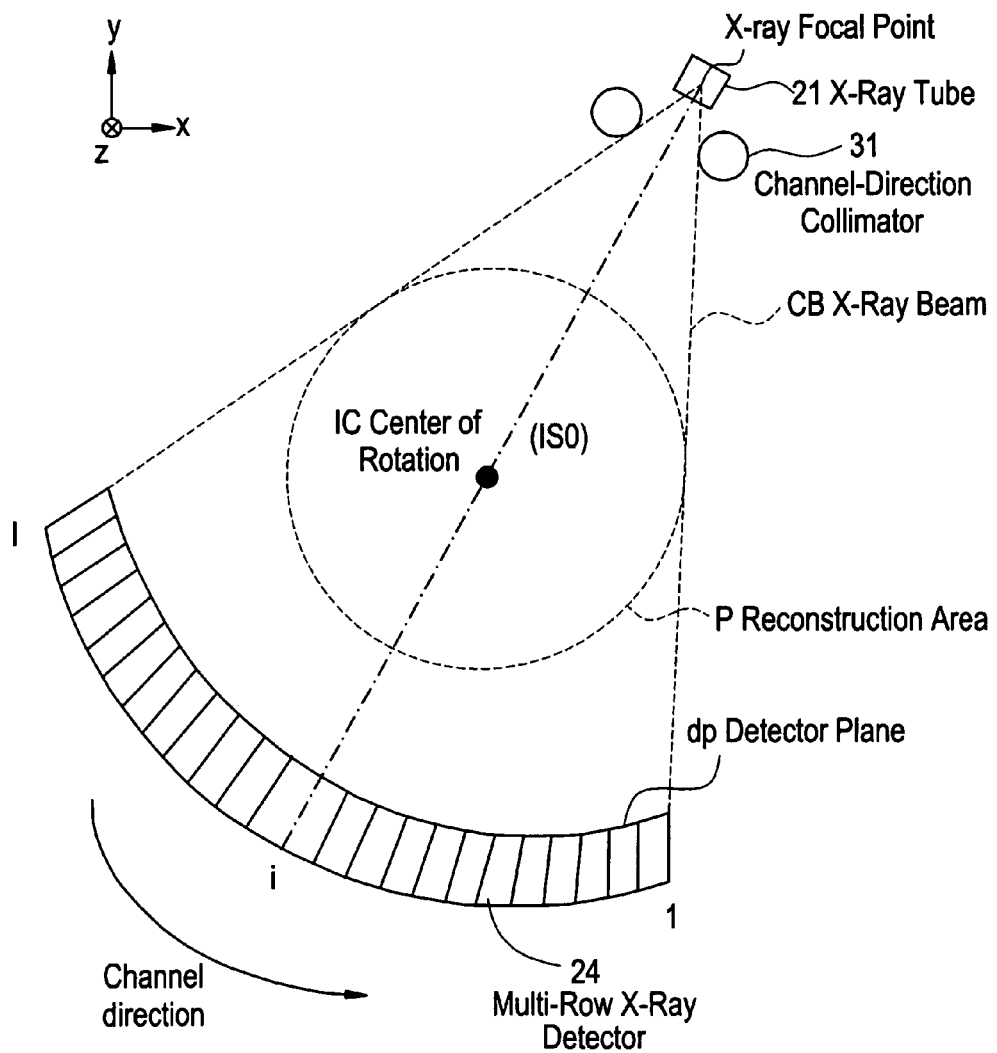
FIG. 2 is an explanatory view illustrating an X-ray generator (X-ray tube) and a multi-row X-ray detector.

FIG. 2 is an explanatory view of a geometric arrangement of the X-ray tube 21 and the multi-row X-ray detector 24.

The X-ray tube 21 and the multi-row X-ray detector 24 rotate about the center of rotation IC. When the vertical direction is defined as a y direction, the horizontal direction is defined as an x direction, and a table traveling direction orthogonal to these is defined as a z direction, the rotational plane of each of the X-ray tube 21 and the multi-row X-ray detector 24 is expressed as an xy plane. The moving direction of the cradle 12 corresponds to the z direction.

The X-ray tube 21 generates an x-ray beam called "cone beam CB". When the direction of a central axis of the cone beam CB is parallel to the y direction, a view angle is assumed to be 0°.

Figure 12:
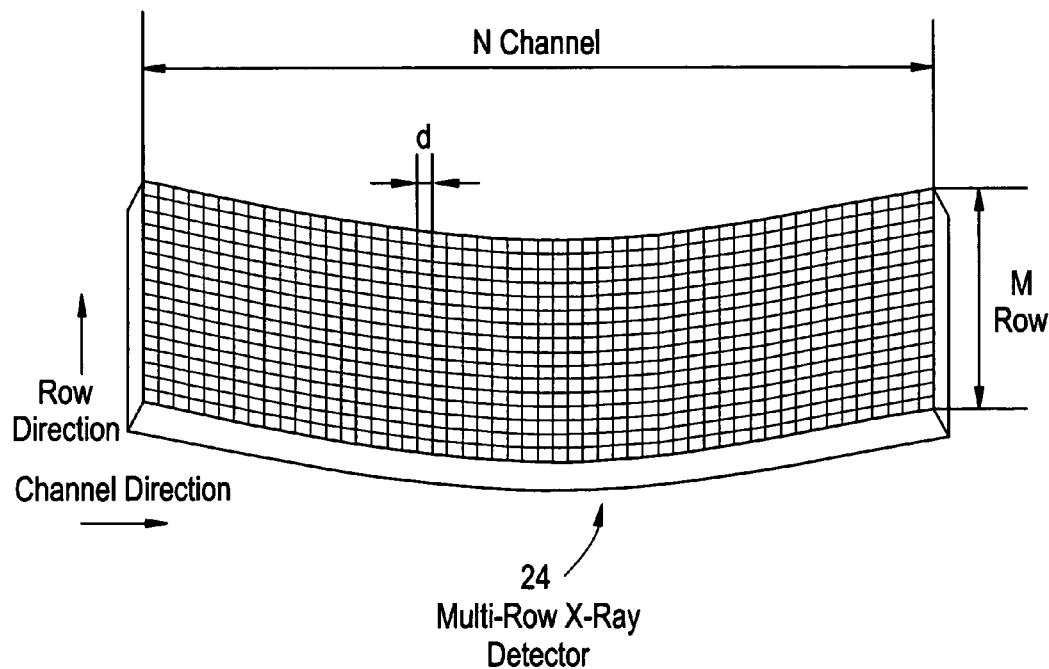
FIG. 12 is a diagram illustrating a conventional multi-row X-ray detector.

The multi-row X-ray detector 24 has detector rows corresponding to 256 rows, for example. The X-ray detector channels each having a constant channel width have heretofore been arranged in the channel direction, and X-ray detector data for all the channels have always been read upon data acquisition, as shown in FIG. 12. In the present embodiment, each detector row has detector channels corresponding to 1024 channels with respect to a data acquisition range and an angle θ in the case of, for example, an X-ray detector channel width d of a data acquiring X-ray detector as shown in FIG. 13. 512 channels equivalent to half of all channels at the central portion of the multi-row X-ray detector 24 are set in such a manner that data can be read even in the case of an X-ray detector channel width d/2 of the data acquiring X-ray detector. In the case of the X-ray detector channel width d/2, each detector row has detector channels corresponding to 1024 channels with respect to a data acquisition range and an angle θ/2.

That is, in the multi-row X-ray detector 24, a plurality of channels which detect X rays transmitted through the subject to acquire or collect X-ray detector data, are respectively arranged in both directions of a channel direction extending along the direction in which they are rotated by a rotational section 15 and a row direction extending along its rotational axis about which they are rotated by the rotational section 15. As shown in FIG. 13, the multi-row X-ray detector 24 has a first area in which a plurality of channels corresponding to a first channel width d/2 are disposed in a channel direction, and second areas in which a plurality of channels corresponding to second channel widths d larger than the first channel width d/2 are disposed in the channel direction. In the multi-row X-ray detector 24, the first area is formed so as to correspond to the central portion as viewed in the channel direction, and the second areas are formed at its peripheral portions so as to interpose the first area therebetween as viewed in the channel direction.

The multi-row X-ray detector 24 and the DAS 25 in this case have two data acquisition modes shown below.

(1) A mode 1 for collecting or acquiring 1024 channels with channel widths d coarse or rough in a data acquisition range (data acquisition range and angle θ) wide as viewed in the channel direction.

(2) A mode 2 for acquiring 1024 channels with a channel width d/2 fine in a data acquisition range (data acquisition angle θ/2) narrow as viewed in the channel direction.

Figures 13A, 13B:
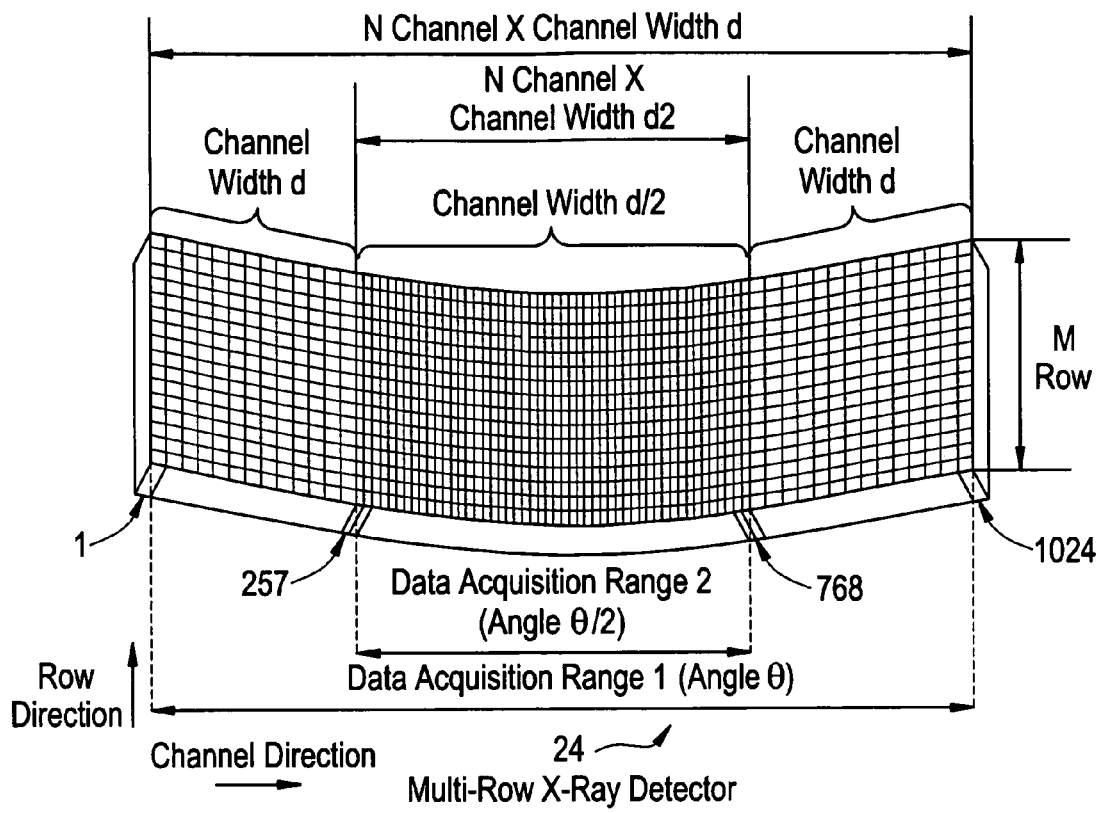
FIGS. 13a and 13b are diagrams showing a multi-row X-ray detector in which a central channel is brought into high resolution.

In this case, the data acquisition system (DAS) 25 effects all-row data acquisition of all 1024 channels on the 1 to 1024 channels shown in FIG. 13(a) with the channel width d upon data acquisition based on the mode 1. Upon data acquisition based on the mode 2, the data acquisition system 25 performs all-row data acquisition of all 1024 channels on the 257 to 768 channels with the channel width d/2.

The data acquisition system (DAS) 25 and the multi-row X-ray detector 24 are electrically connected to each other in such a manner that the data acquisition based on the mode 1 and the data acquisition based on the mode 2 can be conducted. The connection therebetween is switched according to the mode 1 and the mode 2.

Figure 27:
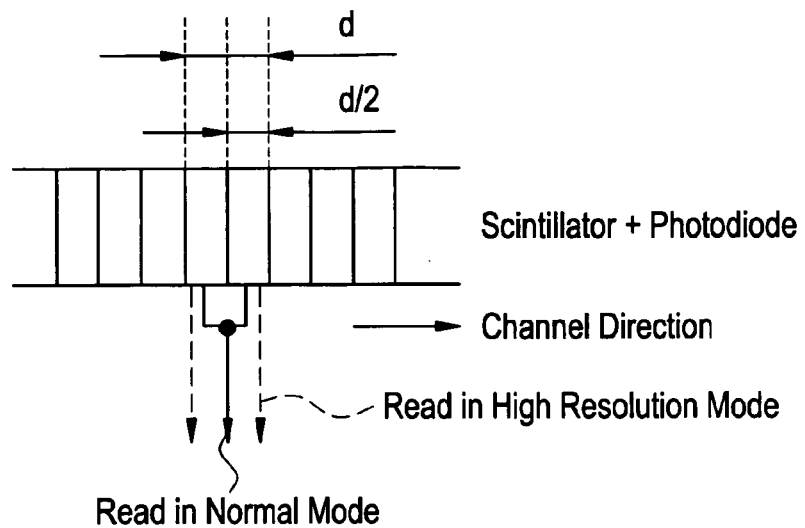
FIG. 27 is a diagram illustrating switching between an X-ray detector channel width d and an X-ray detector channel width d/2.

In the 257 to 768 channels at this time, as shown in FIG. 27, data of X-ray detector channels corresponding to each channel width d/2 are respectively read in the mode 2. In the mode 1, the data of the X-ray detector channels corresponding to each channel width d/2 are respectively added together, after which the added data is read as X-ray detector channel data corresponding to a channel width d.

Figure 28:
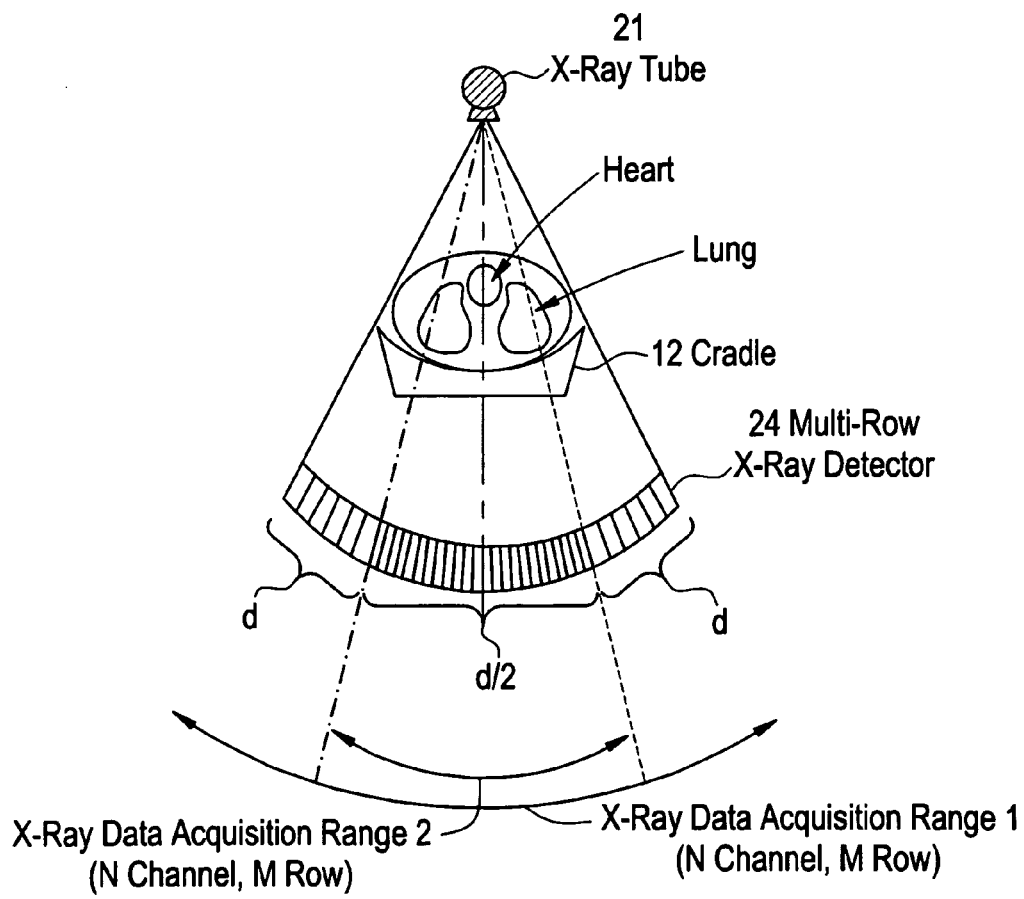
FIG. 28 is a diagram showing switching between a wide data acquisition range and a narrow data acquisition range.

Thus, the data acquisition range wide in the channel direction of the mode 1 and the narrow data acquisition range based on the X-ray detector channels high in resolution as viewed in the channel direction of the mode 2 are used by switching, e.g., the data acquisition range wide in the channel direction of the mode 1 is used for a lung examination and the narrow data acquisition range high in resolution as viewed in the channel direction of the mode 2 is used for a cardiac examination, clinically as shown in FIG. 28, thereby making it possible to use the respective modes effectively.

That is, in the present embodiment, the DAS 25 collects X-ray detector data from the multi-row X-ray detector 24 and outputs the X-ray detector data to the central processing unit 3 via the data acquisition buffer 5. As shown in FIG. 13, the DAS 25 performs switching to an area for acquiring or collecting X-ray detector data so as to collect the X-ray detector data from the channels corresponding to any one of the first area (data acquisition range 2) of the multi-row X-ray detector 24, and the first and second areas (data acquisition range 1). Here, the control controller 29 transmits a control signal, based on a command inputted to the input device 2 from an operator. The DAS 25 performs switching to the area for collecting the X-ray detector data. When the area switching is done such that the X-ray detector data are collected in the first area of the multi-row X-ray detector 24, the DAS 25 acquires or collects X-ray detector data from respective channels arranged in the channel and row directions selected in the first area and outputs the same therefrom. On the other hand, when X-ray detector data are acquired in both of the first and second areas of the multi-row X-ray detector 24, the DAS 25 acquires the X-ray detector data from respective channels arranged in the channel and row directions selected in both the first and second areas and outputs the same therefrom. As to the respective X-ray detector data from the channels of the first area, the DAS 25 adds X-ray detector data from a plurality of channels adjacent to one another in the first area so as to correspond to the channel widths d of the channels in the second areas and outputs the result of addition therefrom. That is, the DAS 25 adds up X-ray detector data from two channels adjacent to each other in the first area so as to become identical to the channel width d for the channels in the second area and outputs it therefrom. Respective X-ray detector data from the channels in the second area are outputted without being added up.

Figure 14:
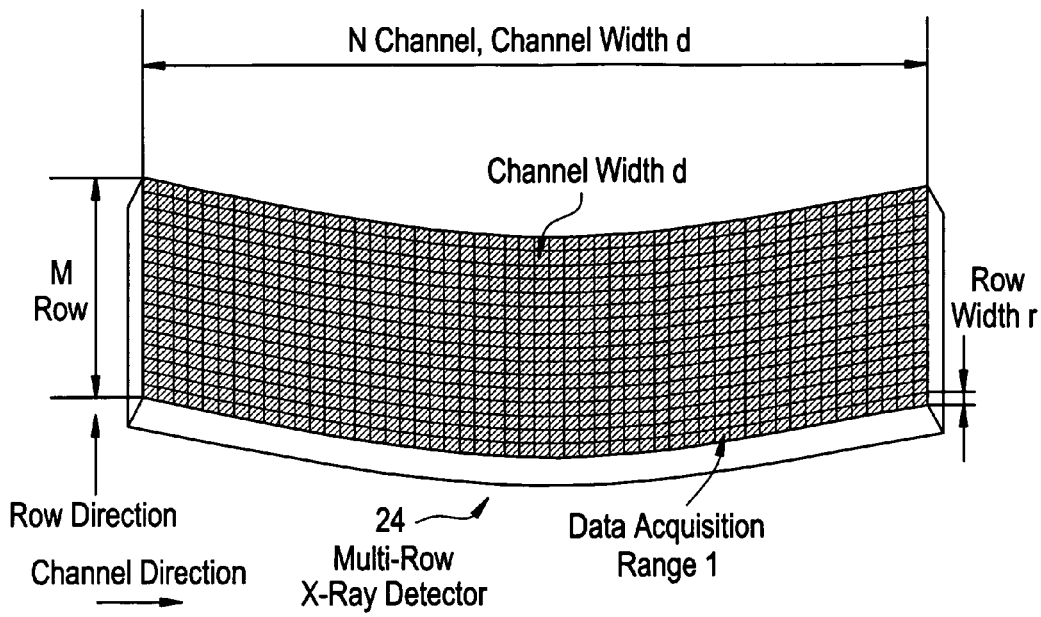
FIG. 14 is a diagram illustrating a conventional data read mode.

The following one is known as another X-ray detector of the present invention. Although the data have heretofore been read over all channels and rows as shown in FIG. 14, the number of reading rows can also be changed depending upon the positions of channels as shown in FIGS. 15, 16, 17 and 18 in one embodiment of the present invention. In this case, data are read in X-ray detector rows small in number at each outer peripheral portion as viewed in the channel direction, and data are read in X-ray detector rows large in number at an inner central portion as viewed in the channel direction. Thus, data acquisition can be performed on the central portion spatially and in high resolution. By collecting some row-direction data at the peripheral portion or non-consecutive data in the row direction or data wide and coarse in row width as viewed in the row direction, a data acquisition number is identical or equivalent to the conventional one, and data acquisition can be effected on the central portion in high resolution as viewed in the channel direction.

X-ray detector data irradiated with X rays and collected are A/D converted by the DAS 25 as viewed from the multi-row X-ray detector 24 and inputted to the data acquisition buffer 5 via a slip ring 30. The data inputted to the data acquisition buffer 5 are processed by the central processing unit 3 in accordance with the program of the memory device 7, after which the data are image-reconstructed as a tomogram or tomographic image, which is displayed on the monitor 6.

Figure 3:
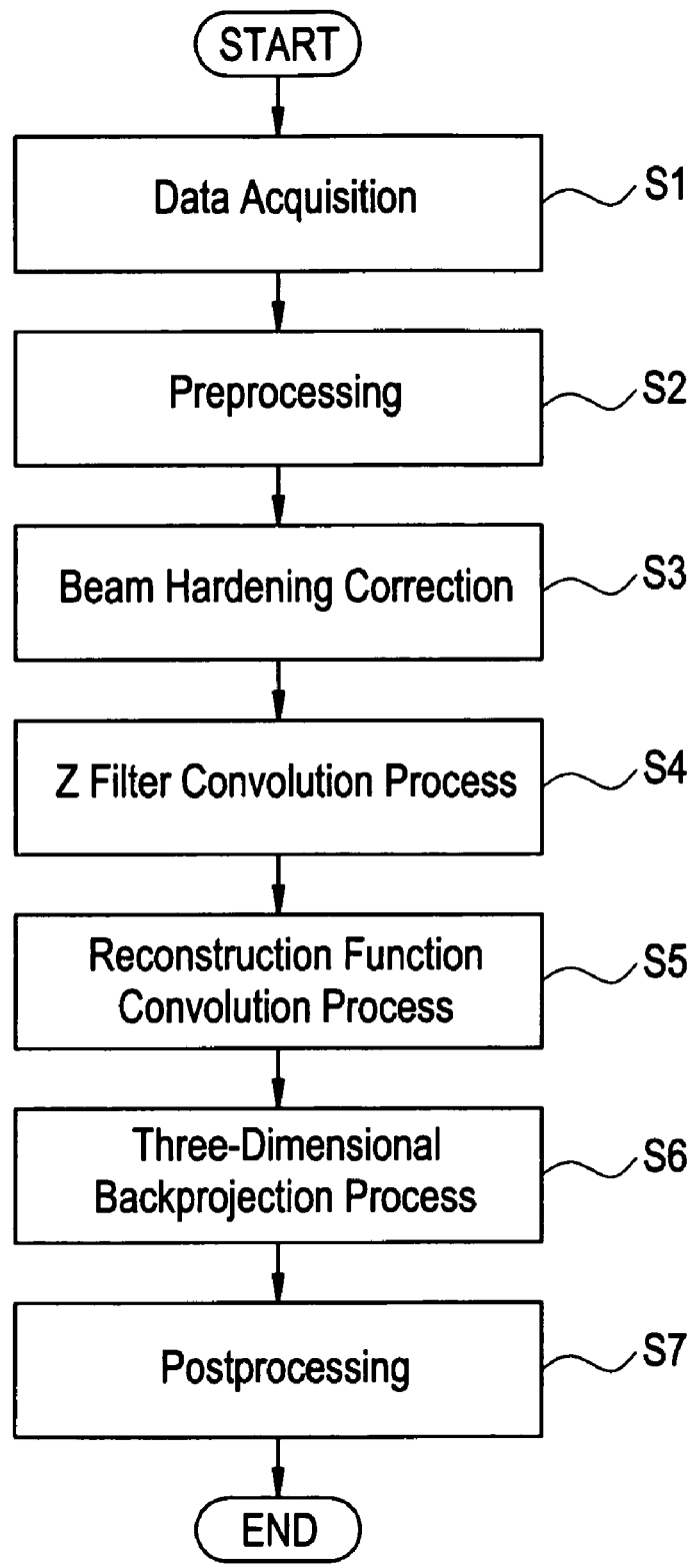
FIG. 3 is a flow diagram depicting a schematic operation of the X-ray CT apparatus according to the one embodiment of the present invention.

FIG. 3 is a flow diagram showing the outline of operation of the X-ray CT apparatus 100 according to the present invention.

In Step S1, the X-ray tube 21 and the multi-row X-ray detector 24 are first rotated about a subject. A helical scan operation is performed while the cradle 12 on the photographing table 10 is being linearly moved. Thus, a table linear movement z-direction position Ztable (view) is added to X-ray detector data D0 (view, j, i) expressed in a view angle view, a detector row number j and a channel number i to collect the X-ray detector data. Upon a conventional scan (axial scan), imaging data are collected with the cradle 12 placed on the photographing table 10 being fixed. In the present embodiment, data acquisition is carried out at fine channel intervals p of (2). Incidentally, the view angle view described above is an angle at which the X-ray tube 21 is rotated and moved about the subject from a predetermined position by the rotational section 15 upon scan's execution. The detector row number j is a number of each detector arranged in the row direction in the multi-row X-ray detector 24. The channel number i is a number of each detector arranged in the channel direction in the multi-row X-ray detector 24. The X-ray detector data D0 (view, j, i) indicate data collected by allowing detectors placed in detector row numbers j and channel numbers i in the multi-row X-ray detector 24 to detect X rays transmitted through the subject when the X-ray tube 21 moved to a predetermined view angle view applies X rays to the subject. The table linear movement Z-direction position Ztable (view) indicates a position where the cradle 12 of the photographing table 10 is moved along the direction of a body axis of the subject upon execution of the scan.

Upon determining the position of the subject, the subject is placed in such a manner that a data acquisition channel interval p at a detector central portion can be used effectively and the subject falls inside a central data acquisition angle θ/2.

Figure 4:
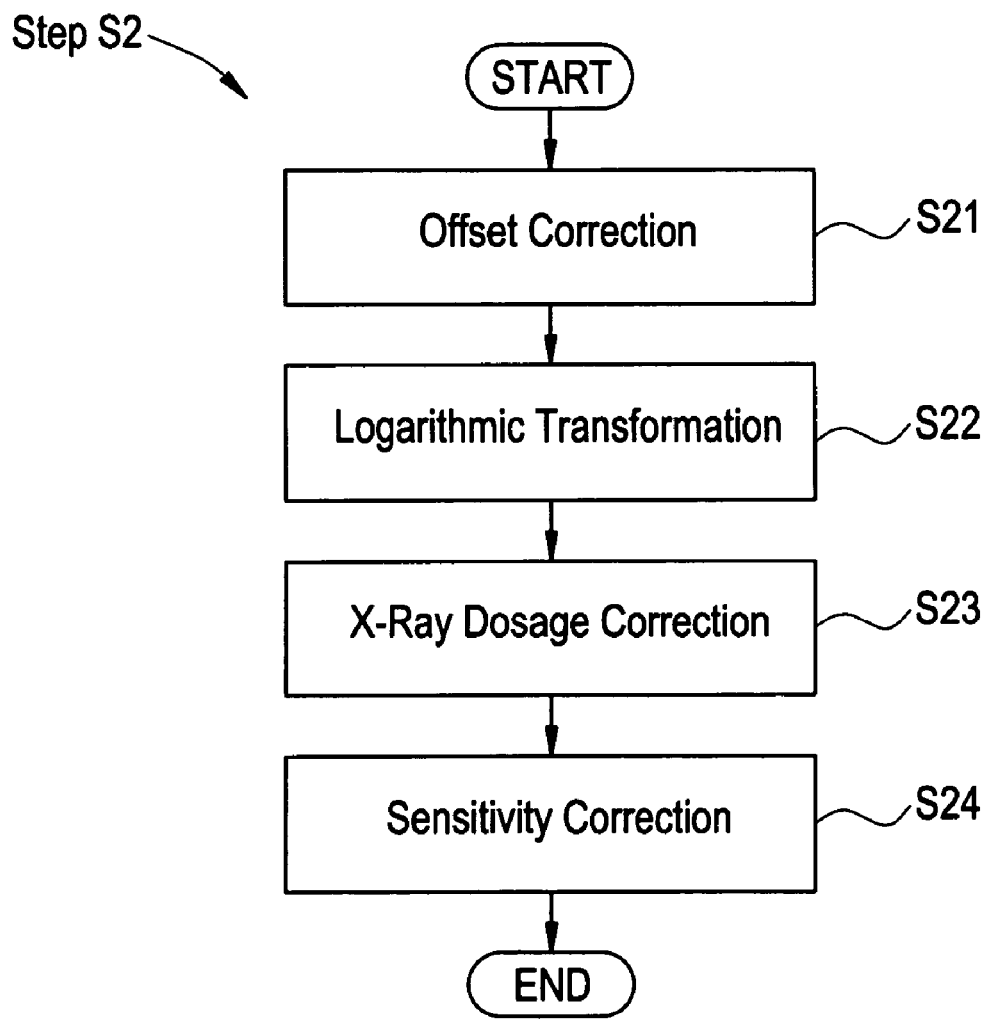
FIG. 4 is a flow diagram showing the details of pre-processing.

In Step S2, preprocessing is effected on the X-ray detector data D0 (view, j, i) and converted to projection data. As shown in FIG. 4, the preprocessing includes an offset correction of Step S21, logarithmic transformation of Step S22, an X-ray dosage correction of Step S23 and a sensitivity correction of Step S24.

In Step S3, a beam hardening correction is effected on pre-processed projection data D1 (view, j, i). Assuming that projection data subjected to the sensitivity correction S24 of the preprocessing S2 is defined as D1 (view, j, i) and data subsequent to the beam hardening correction S3 is defined as D11 (view, j, i) upon the beam hardening correction S3, the beam hardening correction S3 is expressed in, for example, a polynomial form like the following equation (1):

$$D11(\text{view}, j, i) = D1(\text{view}, j, i) \cdot (B_0(j,i) + B_1(j,i) \cdot D1(\text{view}, j, i) + B_2(j,i) \cdot (D1(\text{view}, j, i))^2 \quad (1)$$

Since the beam hardening corrections independent every j rows of the detector can be carried out at this time, the difference between detector's X-ray energy characteristics set every rows can be corrected if tube voltages of respective data acquisition systems are different under photographing or imaging conditions.

In Step S4, a z-filter convolution process for exerting a z-direction (row direction) filter on projection data D11 (view, j, i) subjected to the beam hardening correction is carried out.

In Step S4, after preprocessing at respective view angles and respective data acquisition systems, a filter whose row-direction filter size is 5 rows like, for example, (w1(ch), w2(ch), w3(ch), w4(ch), and w5(ch)) is exerted on projection data of multi-row X-ray detectors D11 (ch, row) (where ch=1–CH, row=1–ROW) subjected to the beam hardening correction in the row direction. Incidentally, ch indicates the channel and row indicates the row herein.

However, the above relation is defined as given by an equation (2) as follows:

$$\sum_{k=1}^{5} w_2(ch) = 1 \quad (2)$$

The corrected detector data D12 (ch, row) is expressed in an equation (3) shown below:

$$D12(ch, j) = \sum_{k=1}^{5} (D11(ch, i-k-3) \cdot w_k(ch)) \quad (3)$$

Incidentally, when the maximum value of the channel is assumed to be CH and the maximum value of the row is assumed to be ROW, they are shown like the following equations (4) and (5):

$$D11(ch, -1) = D11(ch, 0) = D11(ch, 1) \quad (4)$$

$$D11(ch, \text{ROW}) = D11(ch, \text{ROW}+1) = D11(ch, \text{ROW}+2) \quad (5)$$

When a row-direction filter coefficient is changed for each channel, a slice thickness can be controlled according to the distance away from an image reconstruction center. Since the slice thickness becomes thick at a peripheral portion of a tomogram as compared with its reconstruction center in general, row-direction filter coefficients are changed at the central portion and each peripheral portion, the width of each row-direction filter coefficient is widely changed in the neighborhood of a central-portion channel, and the width of each row-direction filter coefficient is narrowly changed in the neighborhood of each peripheral-portion channel. As a result, the slice thicknesses can also be made close evenly even at the peripheral portion and the image reconstruction central portion.

By controlling the row-direction filter coefficients of the central-portion channel and each peripheral-portion channel of the multi-row X-ray detector 24 in this way, the slice thickness can also be controlled at the central portion and the peripheral portion. When the slice thickness is made thick slightly by means of the row-direction filters, both artifacts and noise can be greatly improved. Thus, the degree of an artifact improvement and the degree of a noise improvement can also be controlled. That is, a three-dimensional image reconstructed tomogram, i.e., the quality of an image in an xy plane can be controlled. As another embodiment, a tomogram thin in slice thickness can also be realized by bringing a row-direction (z-direction) filter coefficient to a deconvolution filter.

In Step S5, a reconstruction function convolution process is carried out. That is, data is Fourier-transformed and multiplied by a reconstruction function, followed by being subjected to inverse Fourier-transformation. Assuming that in the reconstruction function convolution process S5, data subsequent to a z filter convolution process is defined as D12, data subsequent to the reconstruction function convolution process is defined as D13, and a reconstruction function to be convoluted is Kernel (j), the reconstruction function convolution process is expressed in an equation (6) shown below:

$$D13(\text{view}, j, i) = D12(\text{view}, j, i) * \text{Kernel}(j) \quad (6)$$

That is, since the reconstruction function kernel (j) can perform a reconstruction function convolution process independent for each j row of the detector, differences in noise characteristic and resolution characteristic for each row can be corrected.

In Step S6, a three-dimensional backprojection process is effected on projection data D13(view, j, i) subjected to the reconstruction function convolution process to determine backprojection data D3(x, y). While the helical scan is being performed in the present invention, an image-reconstructed image is three-dimensionally image-reconstructed to a plane or xy plane orthogonal to the z axis. The following reconstruction area P is assumed to be parallel to the xy plane. The three-dimensional backprojection process will be described later with reference to FIG. 5.

In Step S7, postprocessing such as image filter convolution, CT-value conversion or the like is effected on the backprojection data D3(x, y, z) to obtain a tomographic image or tomogram D31(x, y).

Assuming that a three-dimensionally backprojected tomogram is D31(x, y, z), data subsequent to the image filter convolution is D32(x, y, z) and an image filter is Filter(z), the image filter convolution process corresponding to the postprocessing can be expressed in an equation (7) as follows:

$$D32(x, y, z) = D31(x, y, z) * \text{Filter}(z) \tag{7}$$

That is, since the image filter convolution process independent for each j row of the detector can be conducted, differences in noise characteristic and resolution characteristic for each row can be corrected.

The thus-obtained tomogram is displayed on the monitor 6.

Figure 5:
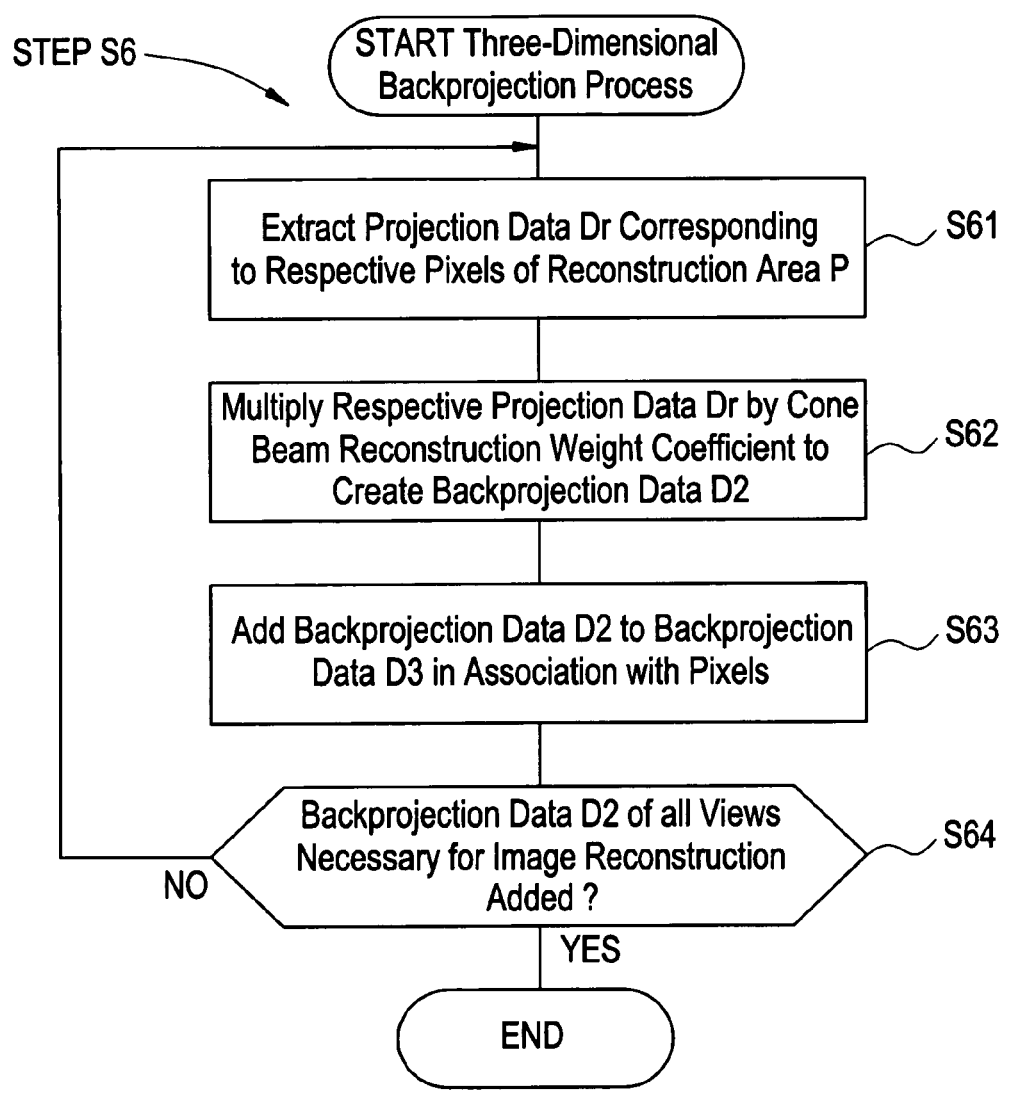
FIG. 5 is a flow diagram illustrating the details of a three-dimensional image reconstructing process.

FIG. 5 is a flow diagram showing the details of the three-dimensional backprojection process (Step S6 of FIG. 4).

In the present embodiment, an image-reconstructed image is three-dimensionally image-reconstructed to the plane or xy plane orthogonal to the z axis. The following reconstruction area P is assumed to be parallel to the xy plane.

In Step S61, attention is paid to one of all views (i.e., views corresponding to 360° or views corresponding to "180°+fan angle") necessary for image reconstruction of a tomogram, and projection data Dr corresponding to each pixel in the reconstruction area P is extracted.

Figure 6B:
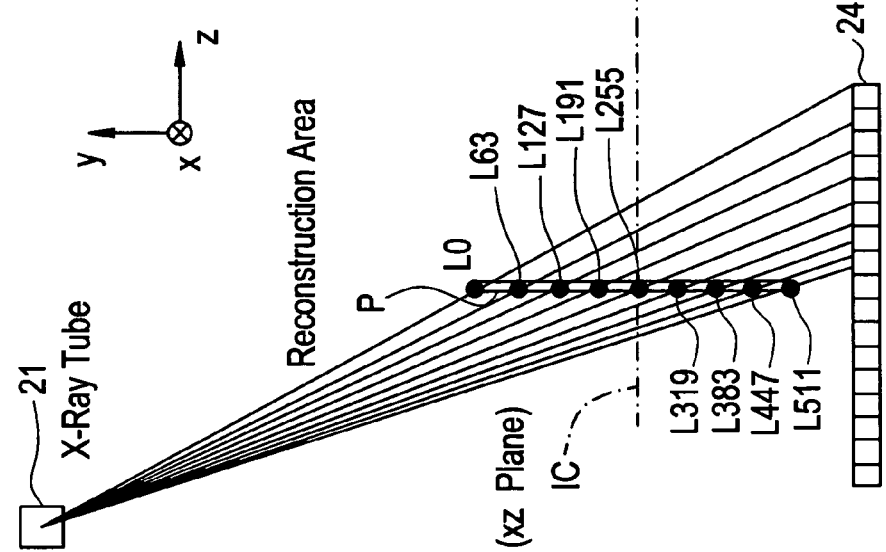
FIGS. 6a and 6b are conceptual diagrams depicting a state of projection of lines on a reconstruction area in an X-ray penetration direction.
Figure 6A:
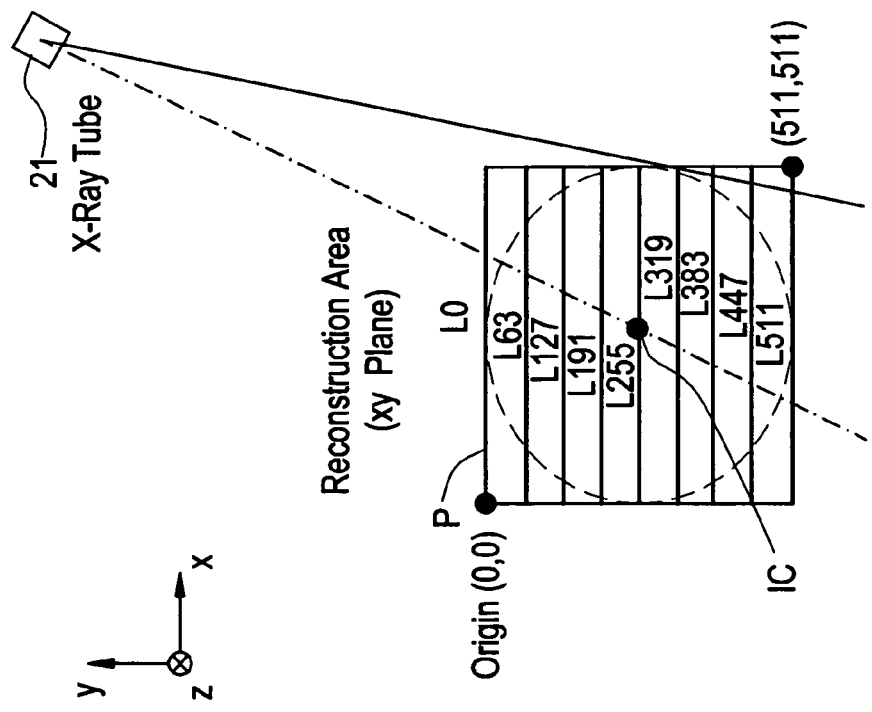
Figure 7:
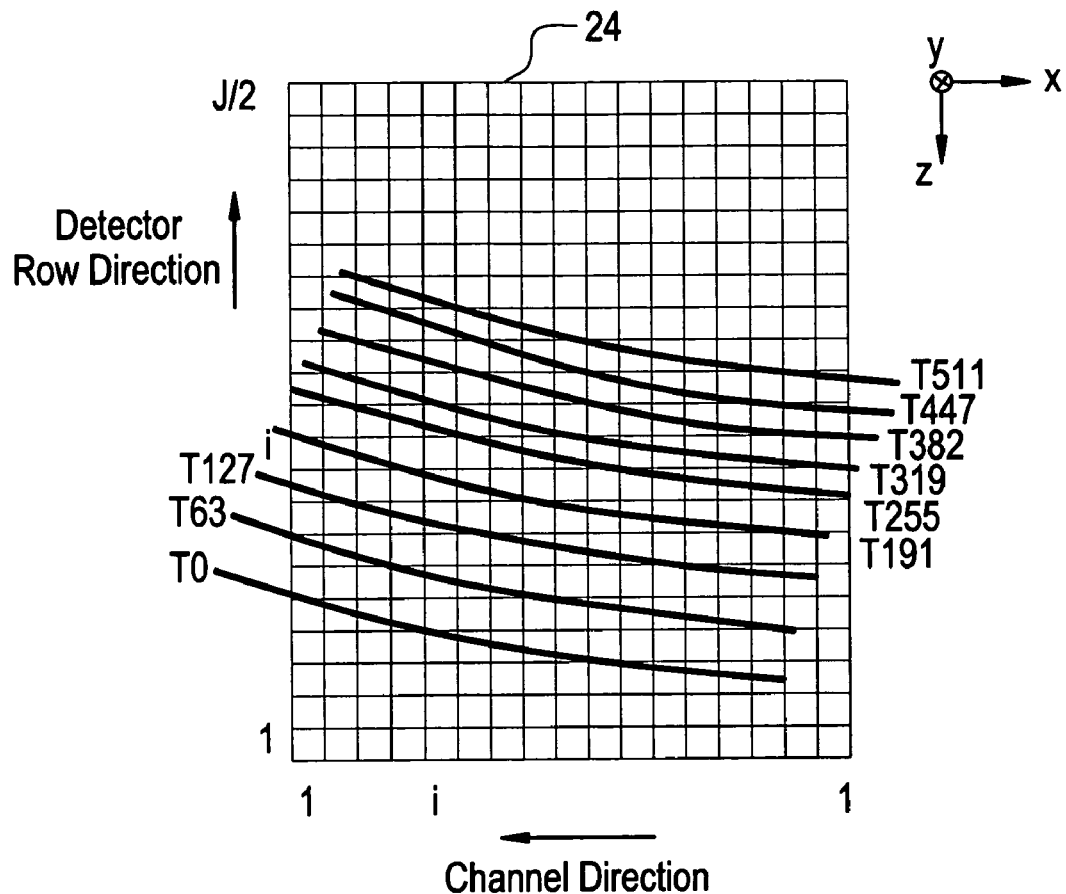
FIG. 7 is a conceptual diagram showing lines projected onto an X-ray detector plane.

As shown in FIGS. 6(a) and 6(b), the area of a square of 512×512 pixels parallel to an xy plane is defined as a reconstruction area P, and a pixel row L0 at y=0, which is parallel to an x axis, a pixel row L63 at y=63, a pixel row L127 at y=127, a pixel row L191 at y=191, a pixel row L255 at y=255, a pixel row L319 at y=319, a pixel row L383 at y=383, a pixel row L447 at y=447, and a pixel row L511 at y=511 are respectively taken as rows. Thus, if projection data on lines T0 through T511 shown in FIG. 7 obtained by projecting these pixel rows L0 through L511 onto the plane of the multi-row X-ray detector 24 as viewed n an X-ray penetration direction are extracted, then they result in projection data Dr(view, x, y) of the pixel rows L0 through L511. However, x and y correspond to each pixel (x, y) of a tomogram.

The X-ray penetration direction is determined depending upon the geometric positions of the X-ray focal point of the X-ray tube 21, the respective pixels and the multi-row X-ray detector 24. Since, however, a z coordinate z(view) of an X-ray detector data D0(view, j, i) is known as a table linear movement z-direction position Ztable(view) concomitantly with X-ray detector data, the X-ray penetration direction can accurately be determined in a data acquisition geometric system of the X-ray focal point and the multi-row X-ray detector even in the case of the X-ray detector data D0(view, j, i) lying in acceleration/deceleration.

Incidentally, when some of each line falls out as viewed in the channel direction of the multi-row X-ray detector 24 as in, for example, the line T0 obtained by projecting the pixel row L0 onto the plane of the multi-row X-ray detector 24 as viewed in the X-ray penetration direction, the corresponding projection data Dr(view, x, y) is assumed to be "0". When it falls out as viewed in the z direction, the corresponding projection data Dr(view, x, y) is determined as extrapolation.

Figure 8:
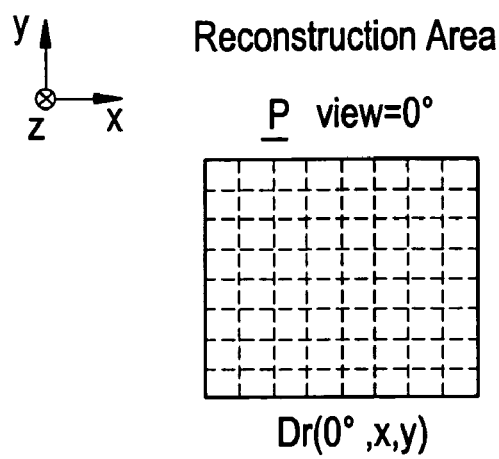
FIG. 8 is a conceptual diagram illustrating a state of projection of projection data Dr (view, x, y) on a reconstruction area.

As shown in FIG. 8, projection data Dr(view, x, y) associated with the respective pixels in the reconstruction area P can be extracted in this way.

Figure 9:
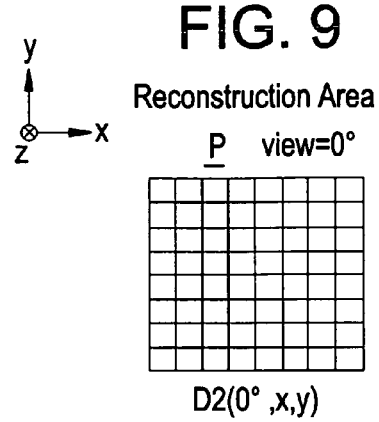
FIG. 9 is a conceptual diagram depicting backprojection pixel data D2 of respective pixels on a reconstruction area.

Referring back to FIG. 5, in Step S62, the projection data Dr(view, x, y) is multiplied by a cone beam reconstruction weight coefficient to create such projection data D2(view, x, y) as shown in FIG. 9.

Here, the cone beam reconstruction weight coefficient w(i, j) is shown as follows. In the case of fan beam image reconstruction, when the angle which a straight line obtained by connecting the focal point of the X-ray tube 21 and each pixel g(x, y) on the reconstruction area P (xy plane) when view=βa forms with a center axis Bc of an X-ray beam, is defined as γ and its opposite beam is defined as view=βb in general, βb results in βb=βa+180°−2γ.

Assuming that the angles which the X-ray beam passing through the pixel g(x, y) on the reconstruction area P and its opposite X-ray beam form with the reconstruction plane P are αa and αb as indicated by the following equation (8), they are multiplied by cone beam reconstruction weight coefficients ωa and ωb dependent upon these and added together to determine backprojection pixel data D2(0, x, y).

$$D2(0, x, y) = \omega a \cdot D2(0, x, y)\_a + \omega b \cdot D2(0, x, y)\_b \tag{8}$$

However, D2(0, x, y)_a is defined as projection data of the view βa, and D2(0, x, y)_b is defined as projection data of the view βb, respectively.

Incidentally, the sum of the cone beam reconstruction weight coefficients with respect to the beams opposite to each other results in ωa+ωb=1.

Multiplying the projection data by the cone beam reconstruction weight coefficients ωa and ωb and adding together makes it possible to reduce cone angle artifacts.

For example, ones determined from the following equations can be used as the cone beam reconstruction weight coefficients ωa and ωb.

When ½ of a fan beam angle is assumed to be γmax, one determined by the equation (14) from the following equation (9) can be used. Incidentally, ga indicates an addition/multiplication coefficient of an X-ray beam in a given direction, and gb indicates an addition/multiplication coefficient of an X-ray beam corresponding to its opposite beam.

$$ga = f(\gamma max, \alpha a, \beta a) \tag{9}$$

$$gb = f(\gamma max, \alpha b, \beta b) \tag{10}$$

$$xa = 2 \cdot ga^q / (ga^q + gb^q) \tag{11}$$

$$xb = 2 \cdot gb^q / (ga^q + gb^q) \tag{12}$$

$$wa = xa^2 \cdot (3 - 2xa) \tag{13}$$

$$wb = xb^2 \cdot (3 - 2xb) \tag{14}$$

Incidentally, for example, q=1 here.

Assuming that max[ ] are functions which take large values, for example, ones determined from the following equations (15) and (16) can be used as examples of ga and gb.

$$ga = \max[0, \{(\pi/2 + \gamma max) - |\beta a|\} \cdot |\tan(\alpha a)|] \tag{15}$$

$$gb = \max[0, \{(\pi/2 + \gamma max) - |\beta b|\} \cdot |\tan(\alpha b)|] \tag{16}$$

In the case of fan beam image reconstruction, each pixel on the reconstruction area P is further multiplied by its corresponding distance coefficient. When the distance from the focal point of the X-ray tube 21 to a detector row j and a channel i of the multi-row X-ray detector 24, corresponding to projection data Dr is r0, and the distance from the focal point of the X-ray tube 21 to each pixel on the reconstruction area P, corresponding to the projection data Dr is r1, the distance coefficient is given as $(r1/r0)^2$.

In the case of parallel beam image reconstruction, each pixel on the reconstruction area P may be multiplied by its corresponding cone beam reconstruction weight coefficient w(i, j) alone.

Figure 10:
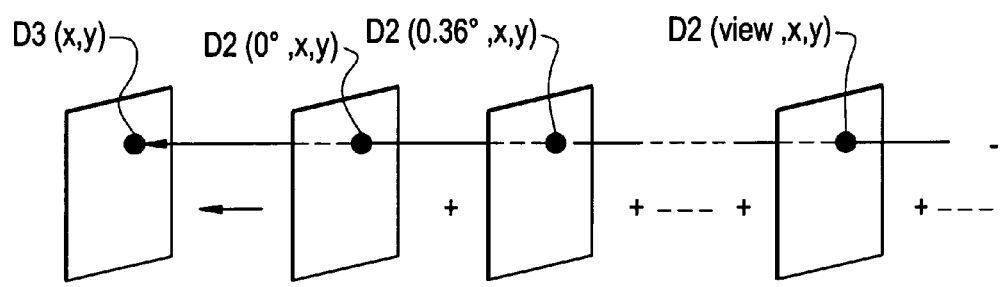
FIG. 10 is an explanatory view showing a state in which backprojection pixel data D2 are added corresponding to pixels over all views to obtain backprojection data D3.

In Step S63, as shown in FIG. 10, projection data D2(view, x, y) is added to backprojection data D3(x, y) cleared in advance in association with each pixel.

In Step S64, Steps S61 to S63 are repeated over all views (i.e., views corresponding to 360° or views corresponding to "180°+fan angle") necessary for image reconstruction of each tomogram, and thereby backprojection data D3(x, y) is obtained as shown in FIG. 10.

Figure 11A:
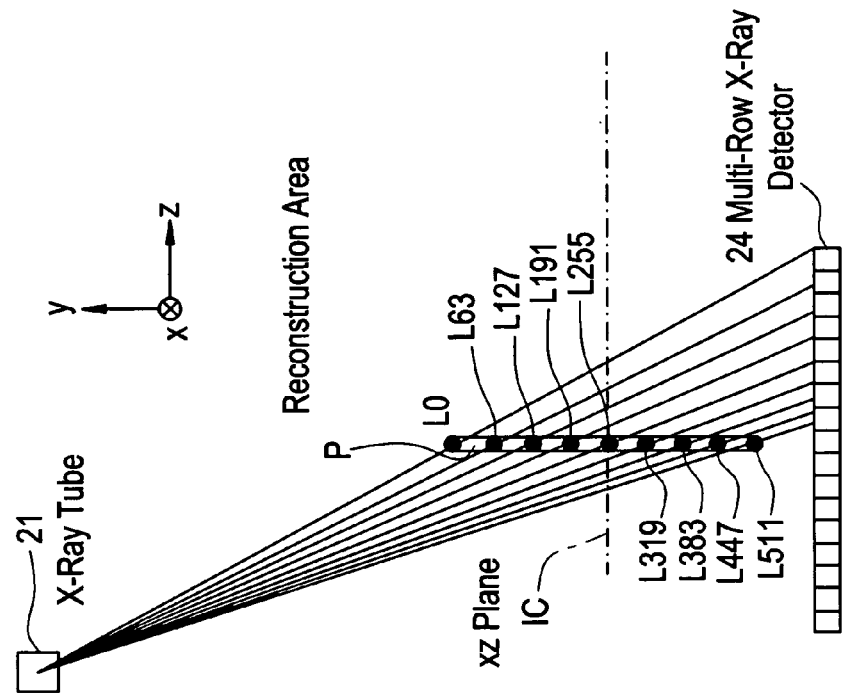
FIGS. 11a and 11b are conceptual diagrams showing a state in which lines on a circular reconstruction area are projected in the X-ray penetration direction.
Figure 11B:
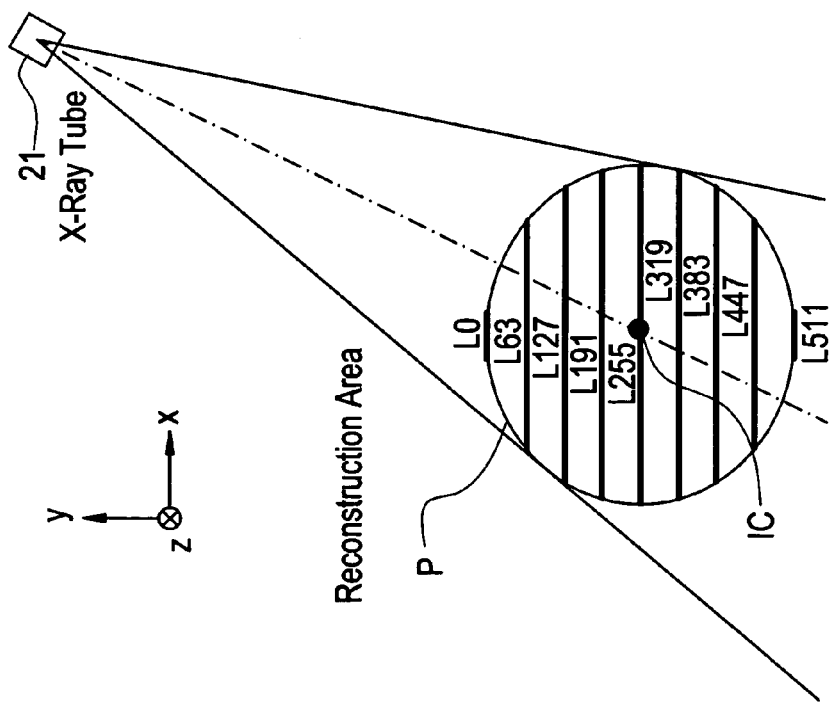

Incidentally, the reconstruction area P may be formed as a circular area as shown in FIGS. 11(a) and 11(b).

The full imaging visual field is normally imaged in the mode of the multi-row X-ray detector 24 with the channel width d as shown in FIG. 12. When, however, a subject small in the imaging field of view is imaged or photographed, data acquisition is performed in the mode in which the central-portion channel is brought to high resolution as shown in FIG. 13, and a tomographic image is created by such image reconstruction as described above.

Since the tomographic image obtained here is image-reconstructed based on projection data acquired at a portion of the multi-row X-ray detector 24 at the time that the fine channel interval is d/2 and the data acquisition angle is θ/2, a tomographic image corresponding to a small imaging area is obtained in high resolution.

Figure 39:
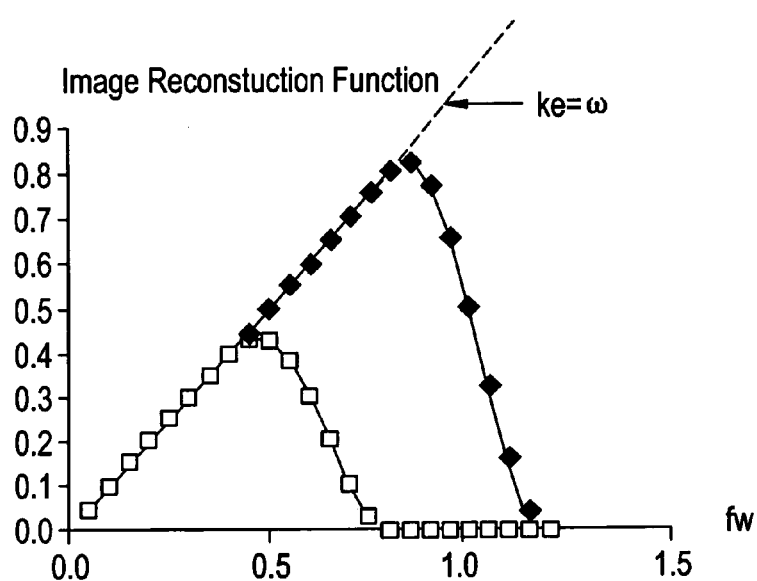
FIG. 39 is a diagram illustrating image reconstruction functions different every X-ray detector channel intervals.

That is, N channels×M rows corresponding to a channel width d in a normal mode, and N channels×M rows corresponding to a channel width d/2 in a high resolution mode can be switched according to a subject. In this case, the data acquisition system (DAS) 25 corresponds to the N channels×M rows and is efficient if N channels corresponding to the channel width d and N channels corresponding to the channel width d/2 are used by switching. If a subject and an area of interest are both small and fall within a range corresponding to an imaging area of N channels×channel width d/2 as shown in FIG. 13, then data acquisition, tomogram image reconstruction and a tomogram image display can be conducted in a high resolution mode based on the N channels× channel width d/2. In the image reconstruction at this time, image reconstruction functions for the normal mode and the high resolution mode are prepared at the reconstruction function convolution process of Step S5 in the flow of such image reconstruction as shown in FIG. 3. When data acquisition is done in the high resolution mode based on the N channels× detector channel width d/2, a Nyquist frequency for sampling at data acquisition increases. Therefore, when the image reconstruction is conducted using the image reconstruction function for the high resolution mode as shown in FIG. 39, a high resolution image whose quality is suitable is obtained.

Incidentally, as the structure of the X-ray detector, the central portion of the X-ray detector as viewed in the channel direction is constituted of scintillators and photodiodes with N channels×channel width d/2 as shown in FIG. 13.

The right and left peripheral portions are respectively constituted of scintillators and photodiodes with N/4 channels× channel width d. When the central N channels×channel width d/2 are read as the high resolution mode, the respective channels corresponding to the channel width d/2 are read independently one by one.

When, however, all channels are read with the N channels× channel width d/2 as the normal mode, the X-ray detector having the respective channels corresponding to the channel width d/2 at its central portion is read in the normal mode with two channels unified into one. Thus, an FET switch is known as a switch for reading the outputs of the scintillators and photodiodes of the X-ray detector by switching.

As shown in FIG. 19, however, the area of interest is small and falls within a range for a high resolution mode with N channels×channel width d/2. When, however, the size of the subject does not fall within the range of the N channels× channel width d/2, the inside of the multi-row X-ray detector 24 as viewed in a channel direction can be data-acquired in a high resolution mode with N channels×channel width d/2 and with M rows×row widths r as viewed in a row direction, whereas the outsides thereof as viewed in the channel direction can be data-acquired in a normal mode with N/4 channels×two points×channel widths d and roughly with M/2 rows×row widths 2r as viewed in the row direction, as shown in FIG. 18, for example. The amount of acquisition of data in the high resolution mode in the case, i.e., the number of data acquired is expressed in the following manner with respect to N channels×M rows in the normal mode:

$$N \text{ channels} \times M \text{ rows} + N/4 \text{ channels} \times 2 \times M/2 \text{ rows} = 1.25 \times N \text{ channels} \times M \text{ rows}$$

The number of channels results in 1.25 times. If a data acquisition time per channel, which is identical to that in the normal mode, is taken, then the total data acquisition time results in 1.25 times. If it is desired to fit the data acquisition time to the same data acquisition time as in the normal mode, then the data acquisition time results in the same data acquisition time as in the normal mode if the data acquisition time per channel is reduced to 0.8 times the data acquisition time in the normal mode.

Thus, even though data acquisition is roughly effected on the outer peripheral portion of the multi-row X-ray detector 24 as viewed in the channel direction, and image reconstruction is further carried out with the resolution of projection data being made rough in the row direction, no influence is exerted on the imaging of the central area of interest in a high resolution mode.

When the detector channel widths d at the channel-direction peripheral portion of the detector and the detector channel width d/2 at the channel-direction central portion of the detector are mixed in data of one row corresponding to one view as shown in FIG. 18, the image reconstruction functions for the high resolution mode are convolved in the reconstruction convolution process of Step S5. Thus, if the image reconstruction function for the high resolution mode corresponding to the detector channel width d/2 is superimposed on the portions of the detector channel widths d, of the peripheral portions, thereby causing image noise more than necessary. This is undesirable to be exact. Avoidance thereof may be handled as follows.

According to the method often used at present, projection data and reconstruction function convolution are Fourier-transformed into a frequency space. The result of multiplication of the projection data and reconstruction functions in the frequency space is inverse Fourier-transformed, followed by being restored to a real space. However, the present method is not capable of using image reconstruction functions in a normal mode different only for the projection data at the peripheral portions of the detector.

Therefore, the image reconstruction functions superimposed or convolved at the detector peripheral portions and the detector central portion may be changed in the real space. The following flow processing may be conducted as shown in FIG. 40.

In Step S51, i, j, view=1. However, i is assumed to be integers of 1 to 1024, j is assumed to be integers of 1 to 256, and view is assumed to be integers of 1 to 1000.

In Step S52, it is determined based on projection data D12(view, j, i) whether a detector channel width is d/2 and is placed in a high resolution mode. If the answer is found to be YES, then the flow processing proceeds to Step S53. If the answer is found to be NO, then the flow processing proceeds to Step S54.

In Step S53, reconstruction functions Kernel HR(j) for the high resolution mode are convolved to determine projection data D13(view, j, i) subsequent to the reconstruction function convolution.

In Step S54, reconstruction functions Kernel LR(j) for the normal mode are convolved to determine projection data D13(view, j, i) subsequent to the reconstruction function convolution.

In Step S55, it is determined whether i=1024. If the answer is found to be YES, then the flow processing proceeds to Step S56.

In Step S56, it is determined whether j=256. If the answer is found to be YES, then the flow processing proceeds to Step S57.

In Step S57, it is determined whether view=1000. If the answer is found to be YES, then the flow processing is completed.

In Step S58, i=i+1 is performed and the flow processing is returned to Step S51.

In Step S59, j=j+1 is executed and the flow processing is returned to Step S51.

In Step S60, view=view+1 is executed and the flow processing is returned to Step S51.

Figure 17:
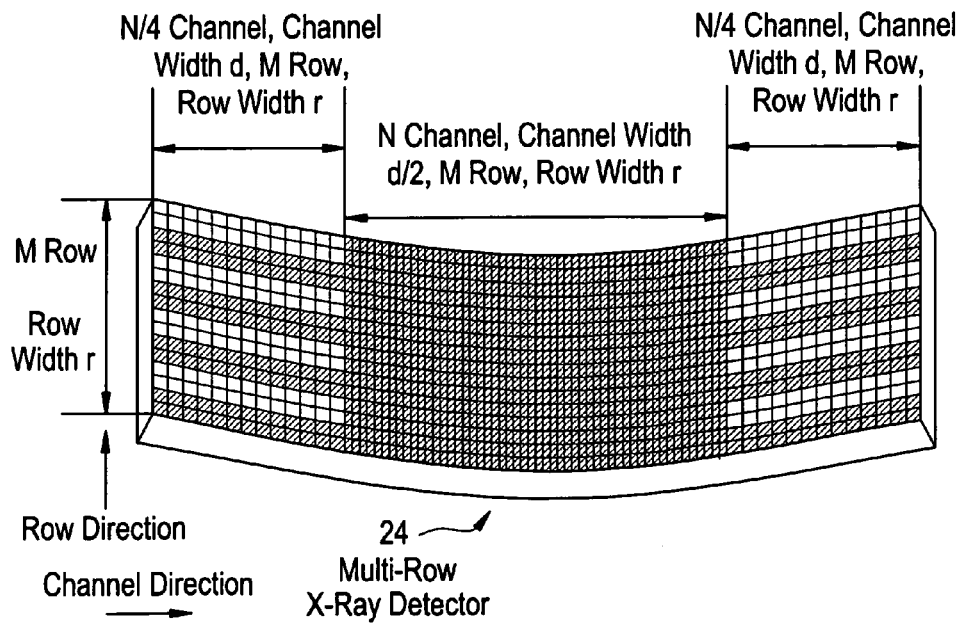
FIG. 17 is a diagram illustrating a mode 3 for reading in the number of rows large at the inner central portion.

The outer portions of the peripheral portions of the multi-row X-ray detector 24 as viewed in the channel direction are data-acquired while the number of the acquired data is being suppressed with the data being bundled in the row direction. As shown in FIG. 17, however, the outer portions of the peripheral portions of the multi-row X-ray detector 24 as viewed in the channel direction may be data-acquired by the M/2 rows with the row widths r at such a thinning-out that the X-ray detector channels per se are placed under the channel width d, M rows and row widths r whereas the data acquisition is placed in N-row skips (data acquisition is placed in two-row skips of N=2 in FIG. 17, for example). In this case, no problem occurs even when projection data at the outer peripheral portions, of the thinned-out and skipped rows are image-reconstructed using data-acquired projection data lying in their adjoining rows. To be exact, the projection data in the row direction are shifted. If, however, the sum of the areas of projection data profiles is not changed suddenly in the z direction, then no influence is exerted on the imaging of an area of interest lying in the center of a tomographic image in a high resolution mode.

Figure 15:
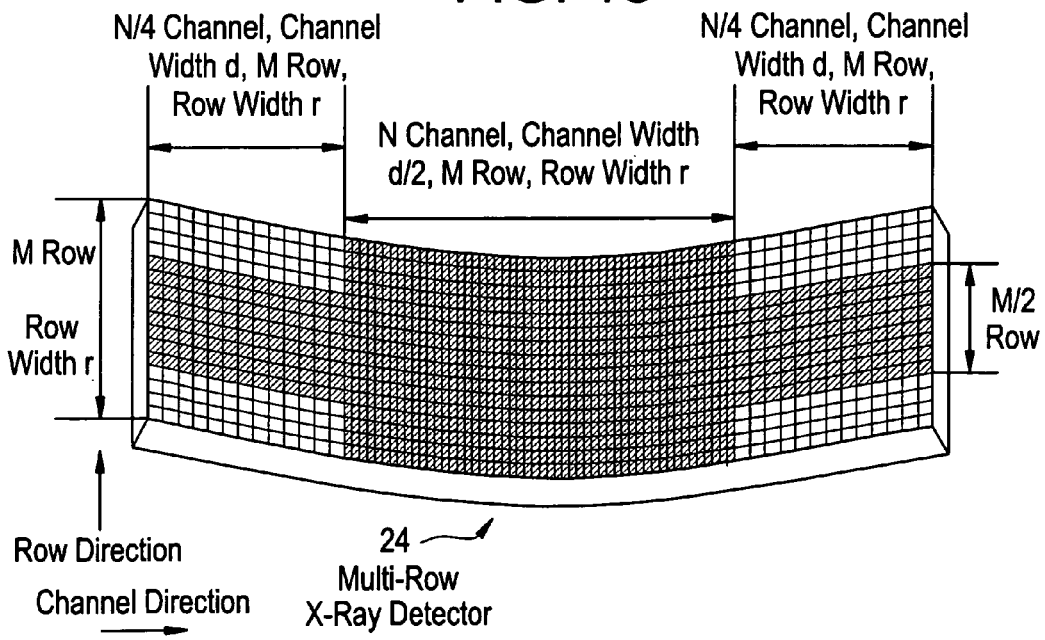
FIG. 15 is a diagram depicting a mode 1 for reading in the number of rows large at an inner central portion.
Figure 16:
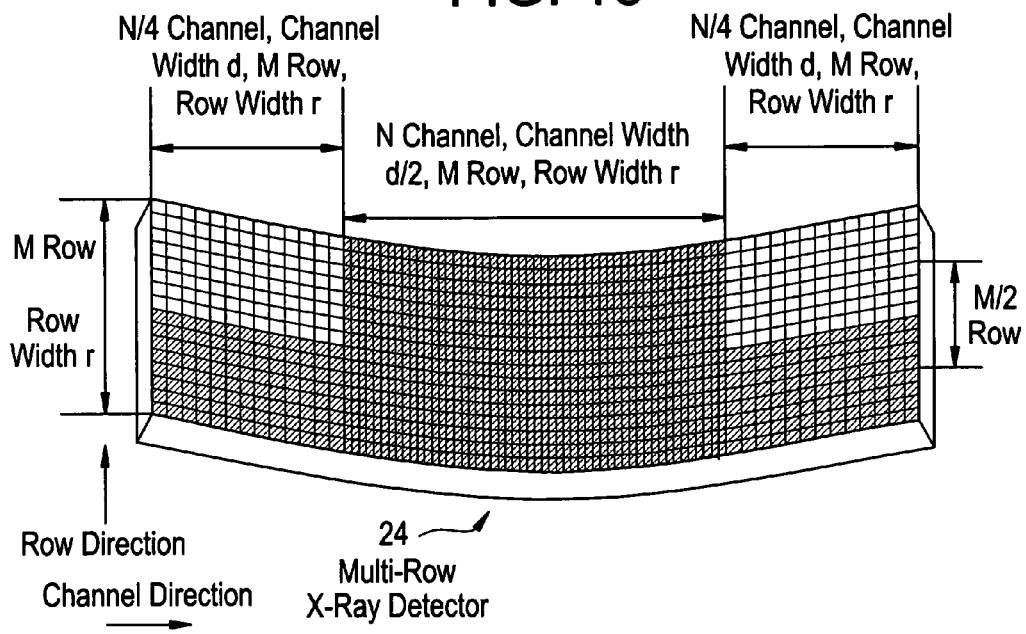
FIG. 16 is a diagram showing a mode 2 for reading in the number of rows large at the inner central portion.

Similarly, as shown in FIG. 16 as an alternative to FIG. 17, thinned-out portions in a row direction are brought together and a data acquisition section may be placed on one side in the row direction. Alternatively, a data acquisition section may be placed in a row-direction center as shown in FIG. 15. If the sum of the areas of the projection data profiles is not changed suddenly in the z direction, then no influence is exerted on the imaging of an area of interest lying in the center of a tomographic image in a high resolution mode.

Thus, as one clinical application that one desires to finely see the central area of interest, may be mentioned, a cardiac examination. Spatial resolution is first required upon the cardiac examination. FIG. 28 shows an example of imaging of a lung field containing the heart. When it is desired to image or photograph the heart inclusive of the lung field, data acquisition, image reconstruction and an image display are carried out in a range including the whole lung field of a subject, using an X-ray data acquisition range 1. As to the data acquisition at this time, data acquisition corresponding to M rows is performed over the X-ray data acquisition range 1 with N channels×X-ray detector channel widths d. Upon imaging specialized for the heart in particular, data acquisition, image reconstruction and an image display are carried out in a range with the heart of the subject as the center, using an X-ray data acquisition range 2. As to the data acquisition at this time, data acquisition corresponding to M rows is performed over the X-ray data acquisition range 2 with N channels×X-ray detector channel width d/2. Next, time resolution is required as the characteristic of the cardiac examination. To this end, the central area of interest is spatially read in a high resolution mode and in satisfactory time resolution at high speed. Further, the rotational section of the scanning gantry 20 is rotated at high speed to make fast a scan time for data acquisition, and the data acquisition may be performed with the same number of data acquisition points.

Figure 24:
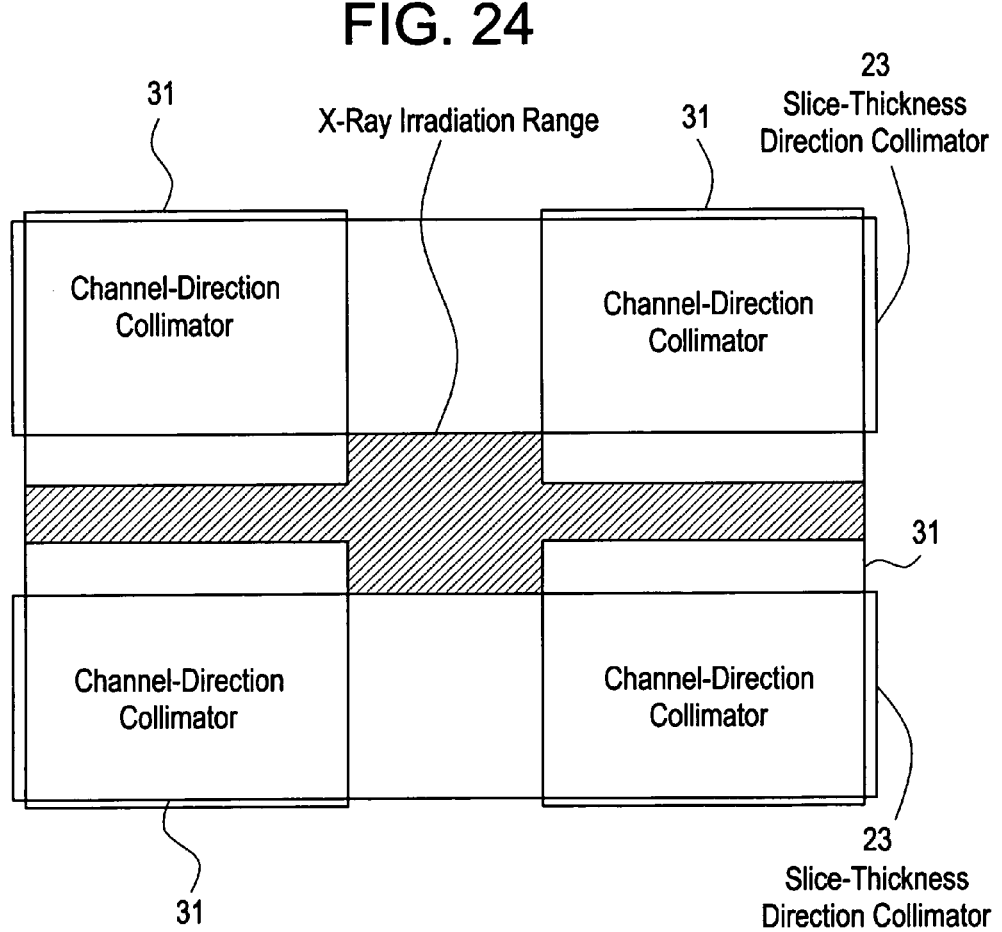
FIG. 24 is a diagram showing an X-ray irradiation range matched with a data acquisition range by a channel-direction collimator.

When the data acquisition ranges in the row direction differ according to the channel positions as shown in FIG. 15 or 16, methods for X-ray controlling X-ray irradiation areas are considered as follows:

(1) Method based on channel-direction X-ray filter (2) Method based on beam forming X-ray filter As shown in FIG. 24, X-ray irradiation areas in a row direction can be controlled so as to differ according to channel positions by channel-direction collimators 31 divided into two in the row direction. Thus, the X-ray irradiation area can be matched with a data acquisition range. Incidentally, FIG. 24 is a diagram showing the direction extending from the X-ray tube 21 to the multi-row X-ray detector 24 as a visual line in FIG. 2.

Figure 25A:
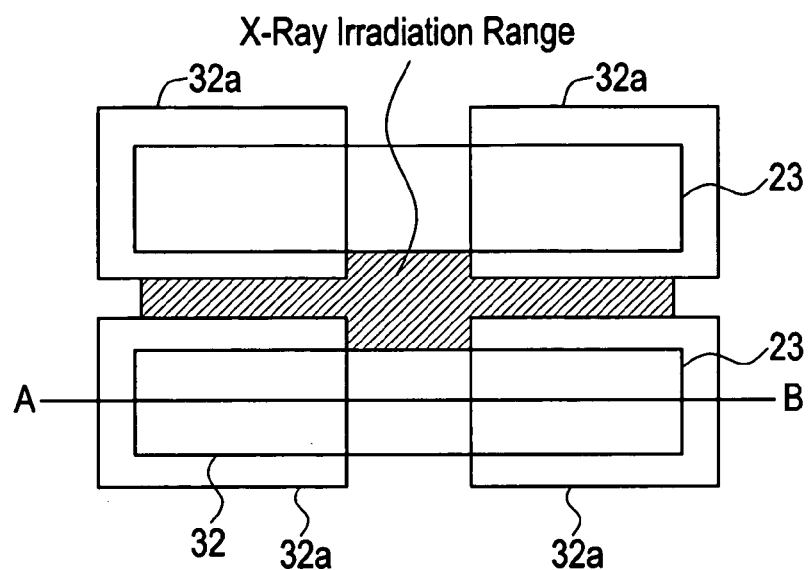
FIGS. 25a, 25b, and 25c are diagrams illustrating a data acquisition range defined by a beam forming X-ray filter.
Figure 25B:
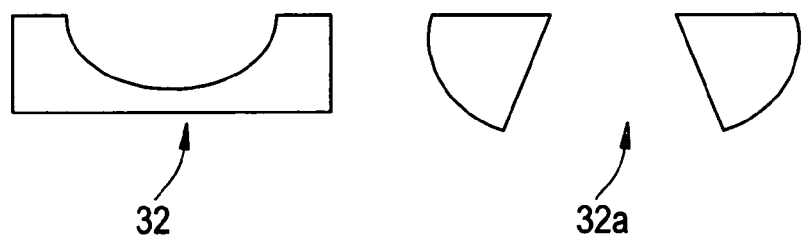
Figure 25C:
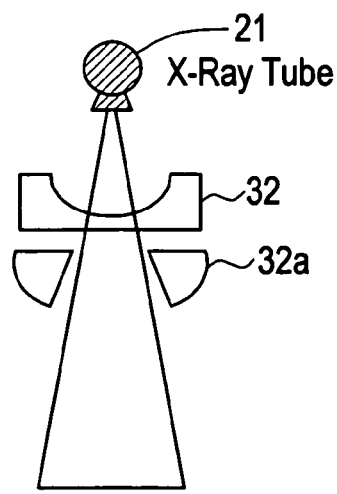

A beam forming X-ray filter 32 and added beam forming X-ray filters 32a overlap as shown in FIG. 25. X-ray irradiation areas in a row direction can be controlled so as to differ according to channel positions. Thus, the X-ray irradiation area can be aligned with a data acquisition range. In FIG. 25, FIG. 25(a) is a diagram showing the direction extending from the X-ray tube 21 to the multi-row X-ray detector 24 as the visual line in FIG. 2, FIG. 25(b) is cross-sectional view showing the beam forming X-ray filter 32 at an A-B section of FIG. 25(a) and the added beam forming X-ray filters 32a, and FIG. 25(c) is a side view showing a layout relationship among the respective portions at the line A-B, respectively.

Figure 26A:
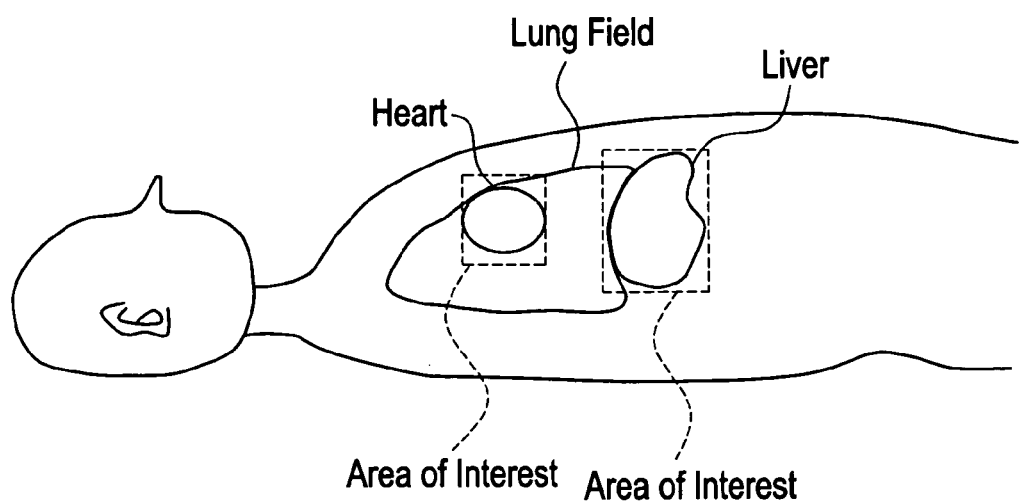
FIG. 26(a) is a diagram showing the setting of areas of interest at scout images as viewed in an RL direction (x direction)
Figure 26B:
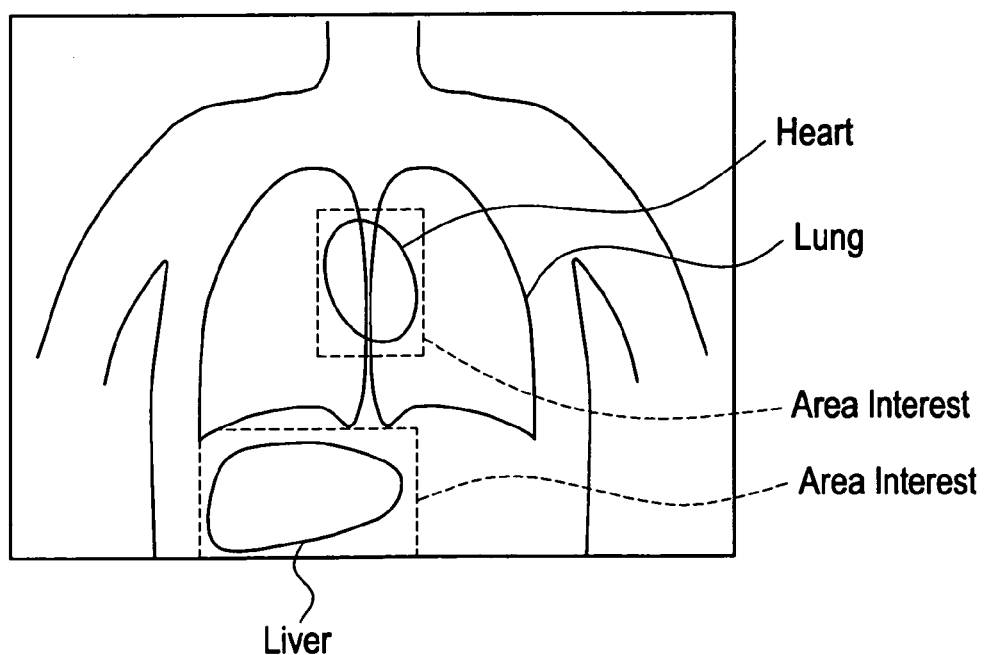
FIG. 26(b) is a diagram showing the setting of areas of interest at scout images as viewed in an AP direction (y direction).

Incidentally, there is a need to match the X-ray irradiation area with a diagnostic area of interest in this case. The diagnostic area of interest may be set on a scout image in advance as shown in FIGS. 26(a) and 26(b) ahead of a scan.

Figure 20:
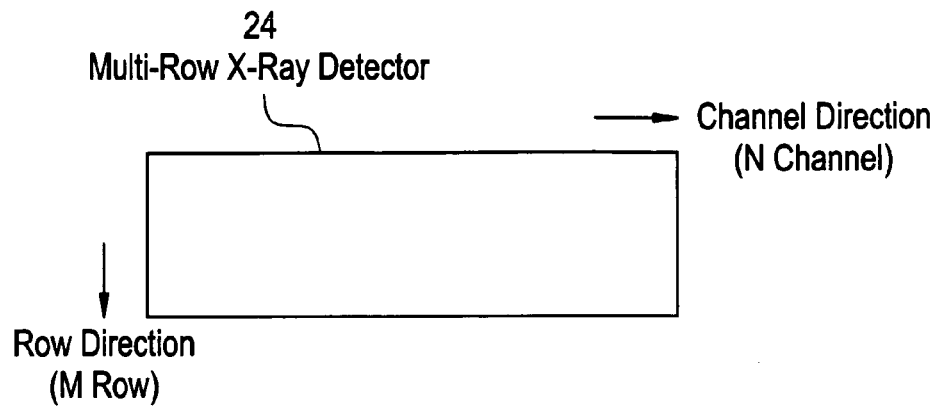
FIG. 20 is a diagram showing a data transfer rate in a normal mode.

FIG. 20 shows the case of reading in a normal mode. Let's assume that the number of channels is L, the number of rows is M, a scan time is T, and the number of views per scan and rotation is L. As one example of an actual scan, N=1024 channels, M=256 rows, scan time T=0.5 s, and the number of views per scan and rotation L=1000 are considered.

A data transfer rate at the reading in the normal mode is expressed as given by the following equation (17):

$$\frac{N \text{ channels} \times M \text{ rows} \times L \text{ view}}{T \text{ seconds}} = \frac{1024 \text{ channels} \times 256 \text{ rows} \times 1000 \text{ views}}{0.5 \text{ seconds}} = \text{about } 500M \text{ (channel/s)} \quad (17)$$

In the normal mode, data is read at this speed.

Figure 21:
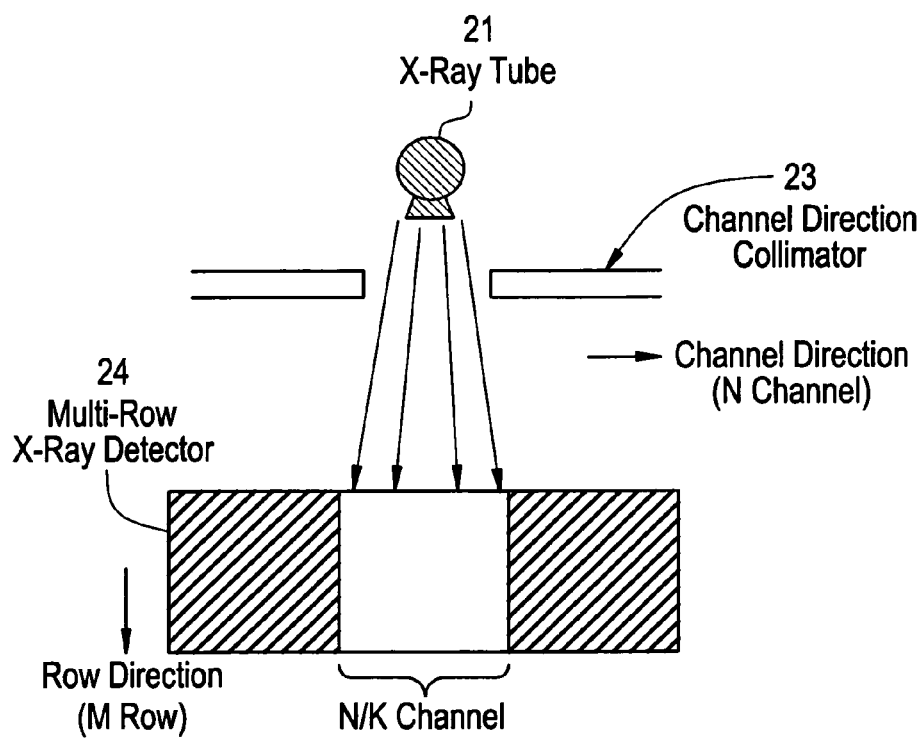
FIG. 21 is a diagram depicting a data transfer rate where data are acquired or collected only at a central portion as viewed in a channel direction.

On the other hand, FIG. 21 shows the idea of a high-speed read mode specialized for the heart in particular.

X rays are controlled by the channel-direction collimator 23 and radiated into a portion corresponding to center N/K channels (512 channels at N=1024 and K=2, for example) of the multi-row X-ray detector 24.

When the portion corresponding to the center 512 channels is n times, e.g., n=0.4, a scan is carried out at nT=0.5 seconds×0.4=0.2 seconds. When the portion corresponding to the central 512 channels is read in this case, data acquisition is carried out at a data transfer rate given by the following equation (18), and image reconstruction and an image display may be performed.

$$\frac{\left(\frac{N}{K}\right) \text{channels} \times M \text{ rows} \times L \text{ view}}{n \cdot T \text{ seconds}} = \frac{\frac{1024}{2} \text{channels} \times 256 \text{ rows} \times 1000 \text{ views}}{0.2 \text{ seconds}} = \text{about } 640M(\text{channel}/s) \quad (18)$$

Incidentally, since the channel-direction collimator 23 is used when the method shown in FIG. 21 is used for the imaging of the heart, a tomographic image whose quality is better is obtained if image reconstruction is carried out using an image reconstruction algorithm for predicting lacked projection data and correcting it, which is shown in an embodiment 2 to be described later.

The portion corresponding to the central 512 channels as viewed in the channel direction is not set to a high resolution mode in the above example. When, however, the portion of the 512 channels corresponding to the X-ray detector channel width d is set to the X-ray detector channel width d/2 with double 1024 channels in the high resolution mode, it is further effective as for the cardiac examination.

When the channels at the central portion are read at this time, data acquisition may be performed at a data transfer rate given by the following equation (19), and image reconstruction and an image display may be conducted.

$$\frac{1024 \text{ channels} \times 256 \text{ rows} \times 1000 \text{ views}}{0.2 \text{ seconds}} = \text{about } 1.25G(\text{channel}/s) \quad (19)$$

Thus, it is known that the X-ray CT apparatus having a plurality of data transfer modes can be adapted to various applications and is effective.

Figure 22:
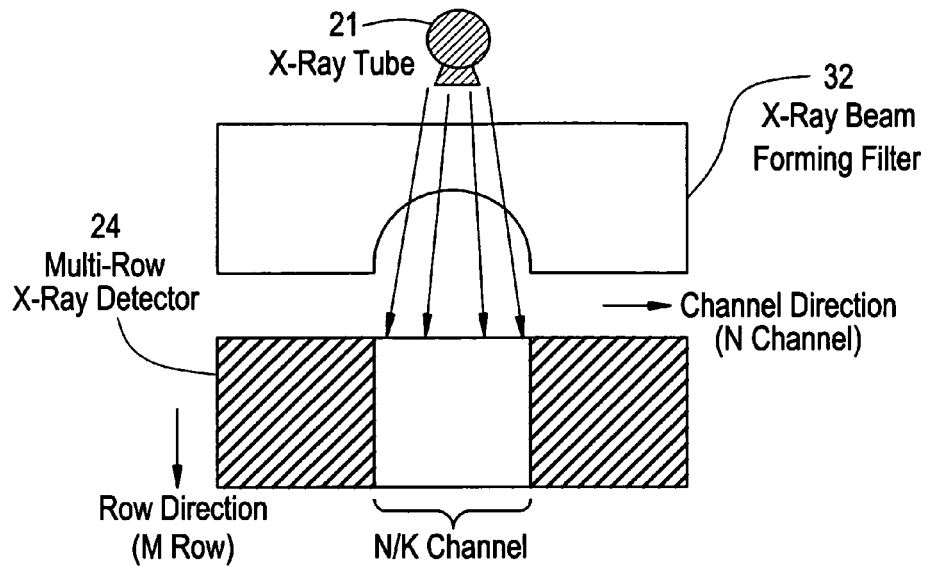
FIG. 22 is a diagram showing a data transfer rate where data are collected only at the central portion as viewed in the channel direction.

FIG. 22 shows an example in which high-speed reading at a channel corresponding to a central portion as viewed in a channel direction is carried out using an X-ray beam forming filter 32.

X rays are attenuated at peripheral portions by the X-ray beam forming filter 32. The X rays are principally radiated into a portion corresponding to center N/K channels (512 channels at N=1024 and K=2, for example) of the multi-row X-ray detector 24.

When the portion corresponding to the center 512 channels is n times, e.g., n=0.4, a scan is carried out at nT=0.5 seconds×0.4=0.2 seconds. When the portion corresponding to the central 512 channel is read in this case, data acquisition is carried out at a data transfer rate given by the following equation (20), and image reconstruction and an image display may be performed.

$$\frac{\left(\frac{N}{K}\right) \text{channels} \times M \text{ rows} \times L \text{ view}}{n \cdot T \text{ seconds}} = \frac{\frac{1024}{2} \text{channels} \times 256 \text{ rows} \times 1000 \text{ views}}{0.2 \text{ seconds}} = \text{about } 640M(\text{channel}/s) \quad (20)$$

Incidentally, since the beam forming X-ray filter 32 is used when the method shown in FIG. 22 is used for the imaging of the heart, a tomographic image whose quality is better is obtained if image reconstruction is carried out using an image reconstruction algorithm for predicting lacked projection data and correcting it, which is shown in the embodiment 2 to be described later.

The portion corresponding to the central 512 channels as viewed in the channel direction is not set to a high resolution mode in the above example. When, however, the portion of the 512 channels corresponding to the X-ray detector channel width d is set to the X-ray detector channel width d/2 with double 1024 channels in the high resolution mode, it is further effective as for the cardiac examination.

When the channels at the central portion are read at this time, data acquisition may be performed at a data transfer rate given by the following equation (21), and image reconstruction and an image display may be conducted.

$$\frac{1024 \text{ channels} \times 256 \text{ rows} \times 1000 \text{ views}}{0.2 \text{ seconds}} = \text{about } 1.25G(\text{channel}/s) \quad (21)$$

Thus, it is known that the X-ray CT apparatus having a plurality of data transfer modes can be adapted to various applications and is effective.

Figure 23:
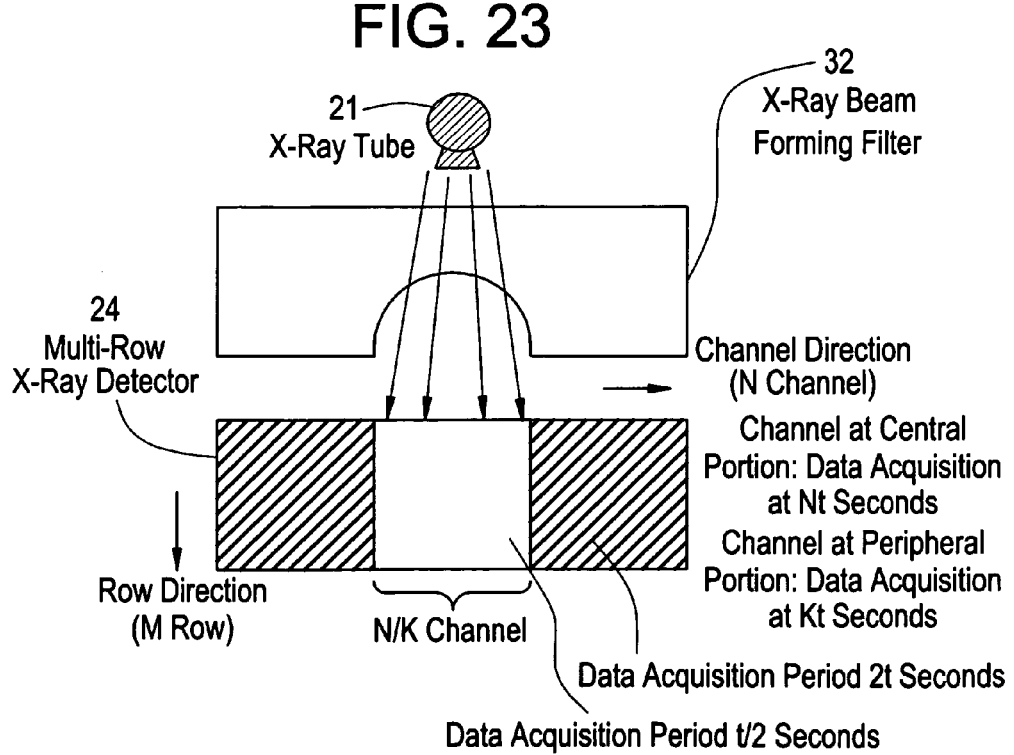
FIG. 23 is a diagram illustrating a multi-row X-ray detector in which a plurality of types of data acquisition sampling periods are provided every data acquisition ranges.

FIG. 23 shows a method wherein since a beam forming X-ray filter 32 is different from the channel-direction collimator 23 and X rays are slightly radiated even into peripheral portions, data obtained in this way are collected and a tomographic image whose quality is better is image-reconstructed.

X rays are principally radiated into a portion corresponding to center N/K channels (512 channels at N=1024 and K=2, for example) of the multi-row X-ray detector 24. When the portion corresponding to the center 512 channels is n times, e.g., n=0.4, data reading is carried out at nT=0.5 seconds×0.4=0.2 seconds. Incidentally, the rate per rotation of the scanning gantry 20 at this time is 0.2 seconds and a scan speed or rate is 0.2 seconds. For example, k=2 in the case of 512 channels at peripheral portions, and data reading is performed at kT=0.5 seconds×2=1.0 second.

When the portion corresponding to the central 512 channel is read, data acquisition is carried out at a data transfer rate given by the following equation (22), and image reconstruction and an image display may be performed.

$$\frac{\left(\frac{N}{K}\right) \text{channels} \times M \text{ rows} \times L \text{ view}}{n \cdot T \text{ seconds}} = \frac{\frac{1024}{2} \text{channels} \times 256 \text{ rows} \times 1000 \text{ views}}{0.2 \text{ seconds}} = \text{about } 640M(\text{channel}/s) \quad (22)$$

Upon the data reading for the 512 channels at the peripheral portions, data acquisition is performed at a data transfer rate given by the following equation (23), and image reconstruction and an image display may be carried out.

$$\frac{\left(N - \frac{N}{K}\right) \text{channels} \times M \text{ rows} \times L \text{ view}}{k \cdot T \text{ seconds}} = \tag{23}$$

$$\frac{1024 - \frac{1024}{2} \text{ channels} \times 256 \text{ rows} \times 1000 \text{ views}}{1 \text{ seconds}} = \text{about } 128M(\text{channel}/s)$$

Incidentally, since the channel-direction collimator 23 is used where the method shown in FIG. 23 is used for the imaging of the heart, a tomographic image whose quality is better is obtained if image reconstruction is carried out using an image reconstruction algorithm for predicting lacked projection data and correcting it, which is shown in the embodiment 2.

The portion corresponding to the central 512 channels as viewed in the channel direction is not set to a high resolution mode in the above example. When, however, the portion of the 512 channels corresponding to the X-ray detector channel width d is set to the X-ray detector channel width d/2 with double 1024 channels in the high resolution mode, it is further effective as for the cardiac examination.

When the channels at the central portion are read at this time, data acquisition may be performed at a data transfer rate given by the following equation (24), and image reconstruction and an image display may be conducted.

$$\frac{1024 \text{ channels} \times 256 \text{ rows} \times 1000 \text{ views}}{0.2 \text{ seconds}} = \text{about } 1.25G(\text{channel}/s) \tag{24}$$

Incidentally, while data about the 512 channels corresponding to the central portion are updated fast at respective views upon image reconstruction at this time, data about the 512 channels at the peripheral portions are updated at low speed. Since, however, the data at the peripheral portions are used to prevent the occurrence of a variation in CT value and artifacts, no influence is exerted on the quality of a high-resolution tomographic image in an area of interest even they are not proper data slightly exactly.

Thus, the existence of data read modes for data acquisition sampling periods different every data acquisition ranges enables adaptation to various applications and provides effectiveness.

As described above, the X-ray CT apparatus 100 according to the present embodiment has the X-ray tube 21 which irradiates the subject with the X rays, the multi-row X-ray detector 24 which detects the X rays irradiated from the X-ray tube 21 and transmitted through the subject, and the rotational section 15 which moves the X-ray tube 21 and the multi-row X-ray detector 24 in such a manner that they rotate about the subject. Based on the projection data obtained by executing such a scan that the X-ray tube 21 rotated about the subject by the rotational section 15 irradiates the subject with the X rays and the multi-row X-ray detector 24 detects the X rays transmitted through the subject, the tomographic image of the subject is image-reconstructed. Here, in the multi-row X-ray detector 24, the plurality of channels which detect the X rays transmitted through the subject to generate the X-ray detector data are respectively arranged in the channel direction extending along the direction in which they are rotated by the rotational section 15, and in the row direction extending along the rotational axis at the time that they are rotated by the rotational section 15. The multi-row X-ray detector 24 has the first area in which the plurality of channels corresponding to the first channel width d/2 are disposed in the channel direction, and the second areas in which the plurality of channels corresponding to the second channel widths d larger than the first channel width d/2 are disposed. In the multi-row X-ray detector 24, the first area is formed so as to correspond to the central portion as viewed in the channel direction, and the second areas are formed at the peripheral portions so as to interpose the first area therebetween. Therefore, the present embodiment is capable of efficiently and easily acquiring an image of desired resolution at a desired data acquisition rate according to imaging conditions.

Embodiment 2

While the embodiment 1 shows the embodiment in which the small imaging area is photographed or imaged in the high resolution, the embodiment 2 shows an embodiment which further realizes low radiation exposure. The embodiment 2 is similar to the embodiment 1 except that the operation of an X-ray CT apparatus 100 is different from that according to the embodiment 1. Therefore, dual portions will not be explained.

Figure 29A:
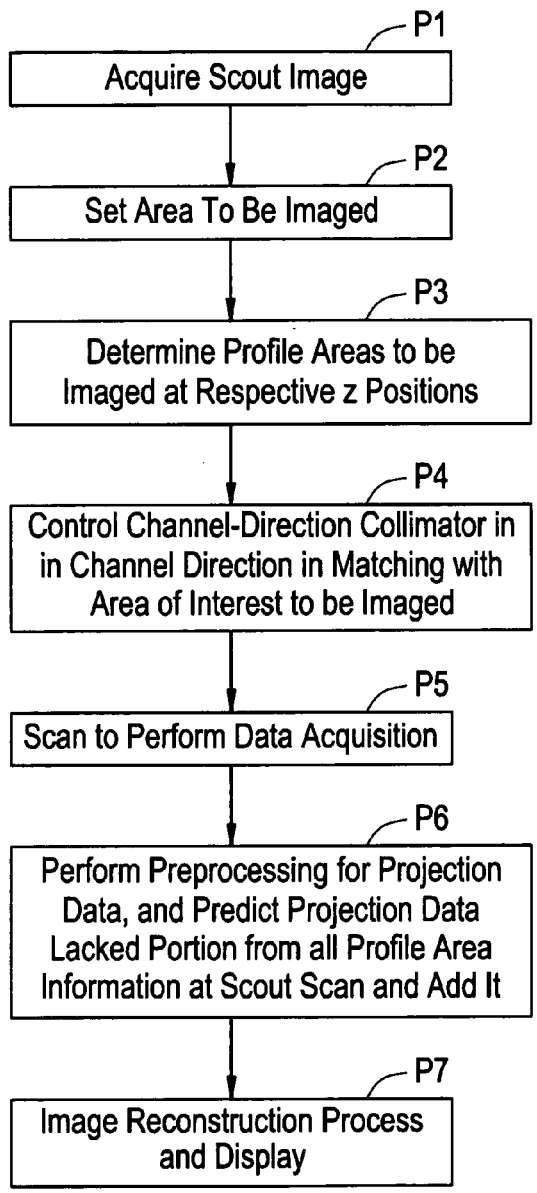
FIGS. 29a and 29b are flow diagrams of the operation of an embodiment 2.
Figure 29B:
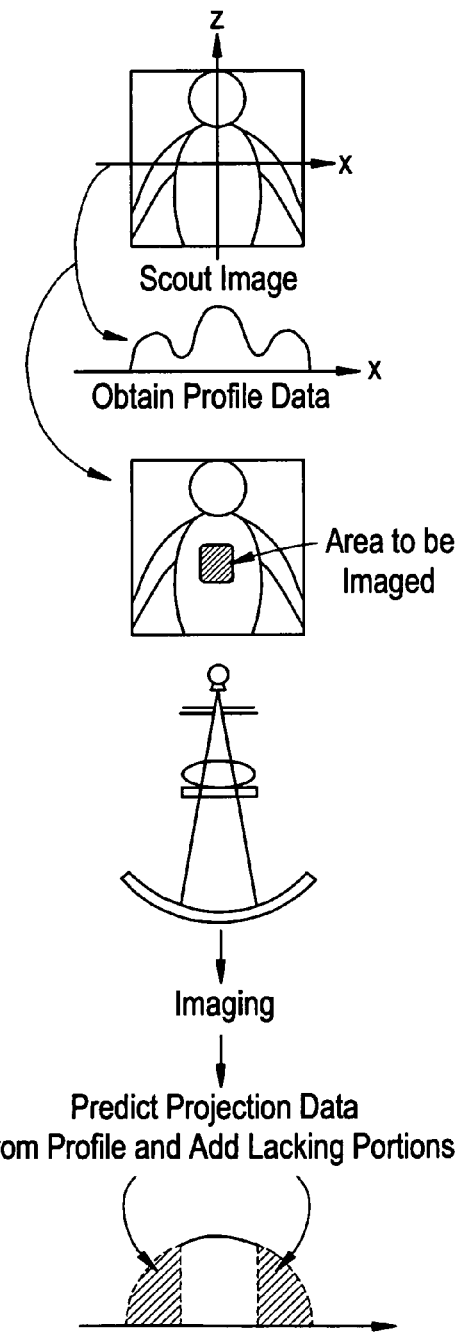

FIG. 29 is a flow diagram showing the outline of operation of the X-ray CT apparatus 100.

The present embodiment will explain an embodiment in which a channel-direction collimator is increased and thereby controlled depending upon the size of FOV that one desires to reconstruct.

Figure 30A:
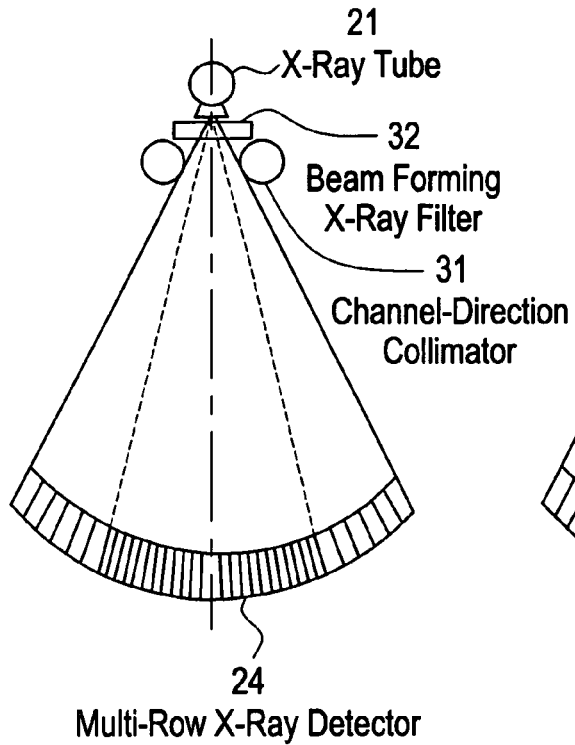
FIG. 30(a) is a diagram showing a channel-direction collimator (rotational-axis eccentric cylindrical system)
Figure 30B:
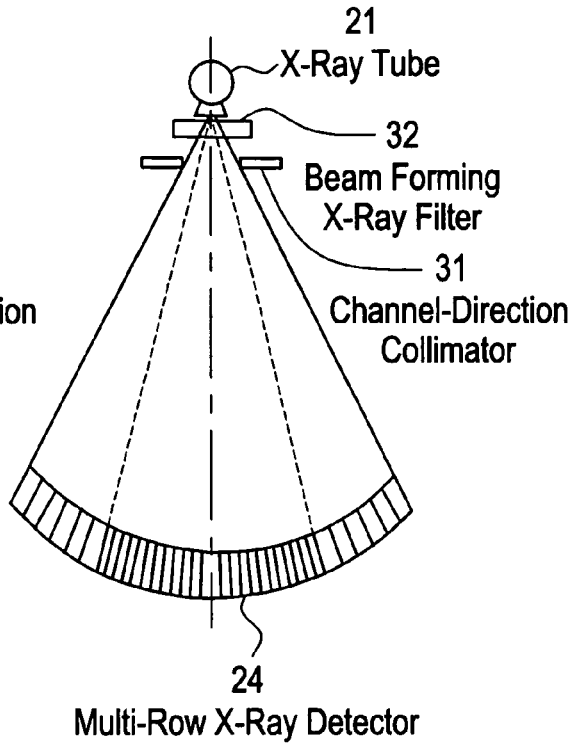
FIG. 30(b) is a diagram showing a channel-direction collimator (shielding plate system)
Figure 30C:
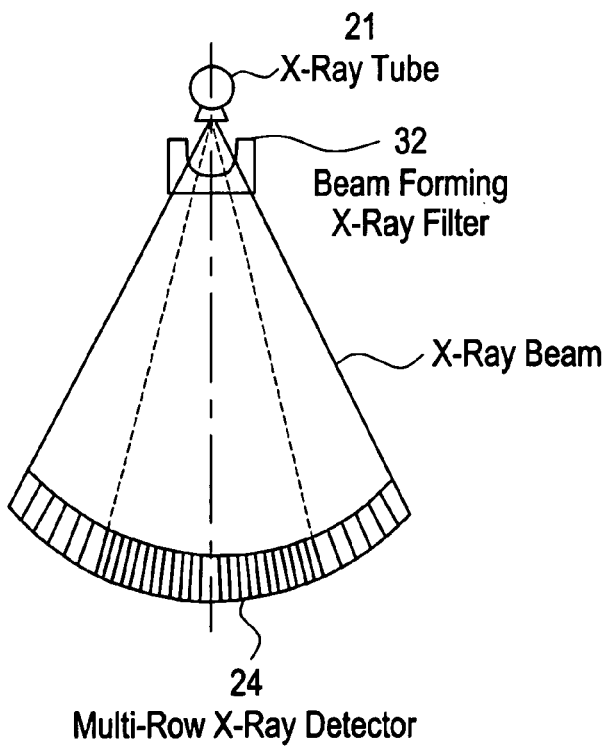
FIG. 30(c) is a diagram showing an example of a beam forming X-ray filter.
Figure 31A:
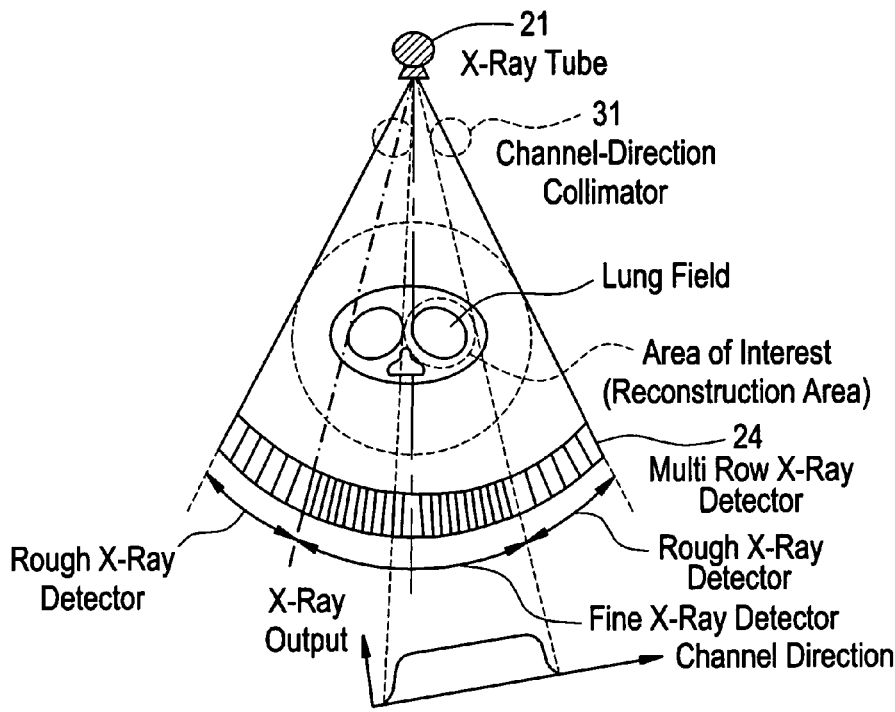
FIGS. 31(a) and 31(b) are respectively diagrams showing channel-direction collimator control.
Figure 31B:
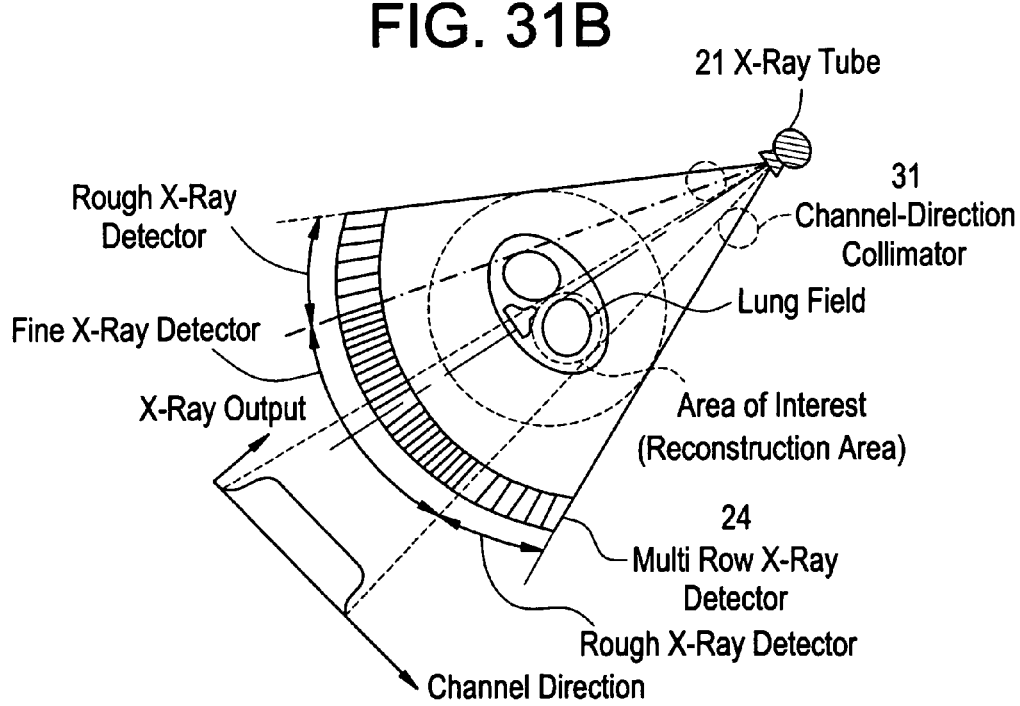

Although a shielding plate system (plate-shaped collimator system) (FIG. 30($a$)) and a shielding cylindrical system (rotational-axis eccentric columnar collimator system) (FIG. 30($b$)) are considered as collimators, either can be used in the present embodiment. The z-direction collimator (slice thickness direction) control has been controlled by allowing the DAS 25 to read the data of the z channel, whereas in the channel-direction collimator 31, the positions of X rays radiated into the multi-row X-ray detector 24, which are determined depending upon an angle β (view angle β) of an X-ray data acquisition system, and the position and size of an area of interest to be photographed, are determined in advance. An aperture position and width of the channel-direction collimator 31 are feedforward-controlled based on the positions. Further, feedback control in the channel direction is performed as needed based on the value of each main detector channel of the DAS 25 which performs projection data acquisition (refer to FIGS. 31($a$) and 31($b$)).

With the advance of performance of a CPU for DAS control and a CPU for collimator control, calculations for reading the main detector channel corresponding to the data of the multi-row X-ray detector 24 and performing the feedback control on the aperture of the channel-direction collimator are considered not to substantially cause a problem. When SN of X-ray data is not ensured with respect to a fat patient, only feedback control may be performed in accordance with a channel-direction collimator position predicted based on the position/size of an imaging field of view in advance.

A drive system or the like such as a pulse motor which controls a collimator operation in this case, is also considered to have a sufficient response speed.

In the whole flow shown in FIG. 29, a small imaging area can be photographed in high resolution and with good image quality through the subsequent flows.

In Step P1, data acquisition of a scout image is first performed.

In Step P2, an area to be imaged or photographed on the scout image is set.

In Step P3, profile areas at respective z positions to be imaged are determined.

In Step P4, the channel-direction collimator is controlled in the channel direction in matching with an area of interest to be imaged.

In Step P5, a scan is performed to carry out data acquisition.

In Step P6, preprocessing for projection data is performed to obtain all profile area information at the respective z positions subjected to the scout scan. The channel-direction collimator predicts a projection data portion lacked at each peripheral portion as viewed in the channel direction and adds it thereto.

In Step P7, an image reconstruction process and an image display are performed using the projection data added with the lacked portion.

Figure 32A:
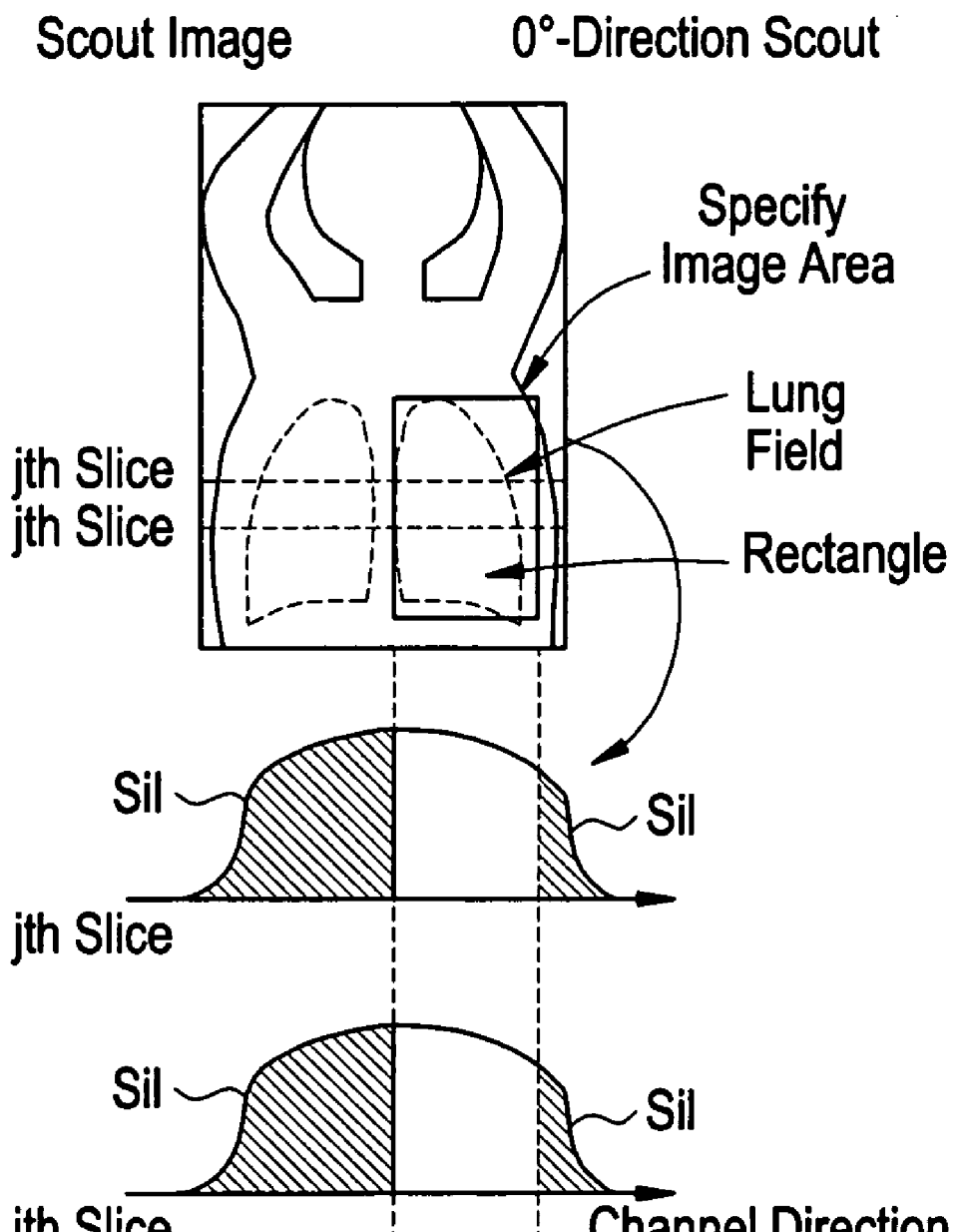
FIGS. 32a, 32b, and 32c are diagrams illustrating the manner in which projection data that lack at a channel-direction X-ray collimator are added.
Figure 32B:
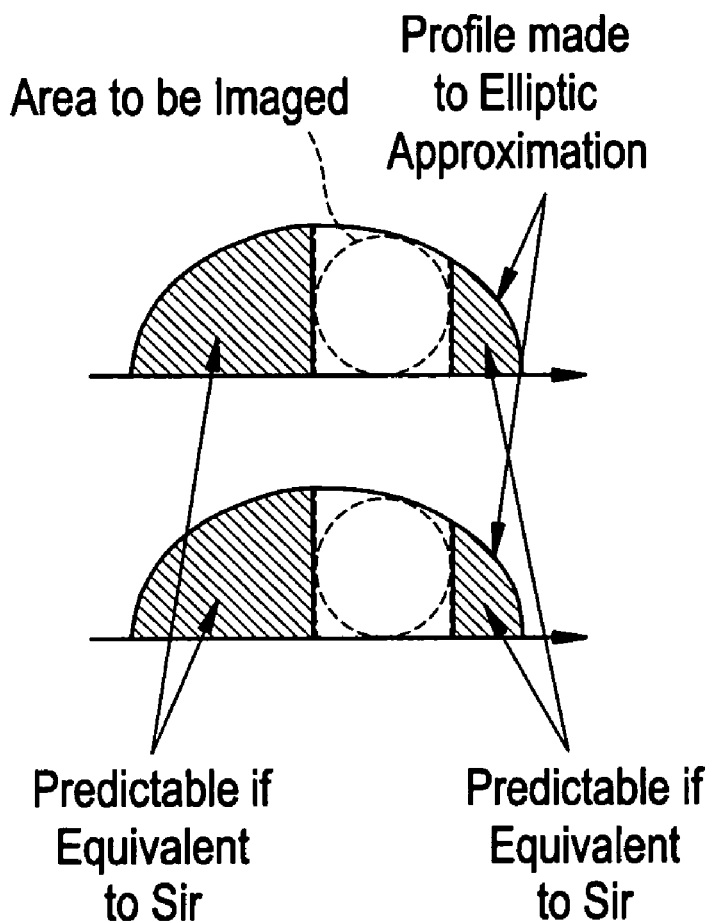
Figure 32C:
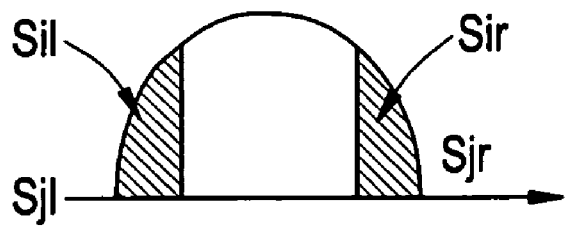

When X rays other than at a portion to be imaged are shielded by the channel-direction X-ray collimator as shown in FIG. 32, there is a need to predict projection data corresponding to the shield portion. As shown in FIG. 32(b) here, projection data are predicted in accordance with a relationship of position between profiles obtained by allowing the areas of Sil, Sir, Sjl and Sjr in respective directions at the time that they are rotated by 360°, to make elliptic approximations, and an imaging area. Incidentally, projection data may be added to both sides in the form of triangular approximations or circular approximations as shown in FIG. 32(c).

The feedforward control of the channel-direction X-ray collimator will be explained using a flowchart of FIG. 33.

In Step C1, an angular range (from the minimum irradiation channel γmin to the maximum irradiation channel γmax) or a channel range on the multi-row X-ray detector 24 to radiate X rays is determined by calculation according to an angle β (view angle β) of an X-ray data acquisition system comprised of the X-ray tube 21, multi-row X-ray detector 24 and DAS 25, and the size and position of an imaging area of interest (e.g., a circular area of interest whose center is (xo, yo) and whose radius is R).

In Step C2, the channel-direction collimator (which may be an eccentric cylindrical collimator or a shielding plate-like collimator) is made open from the minimum irradiation channel γmin to the maximum irradiation channel γmax.

In Step C5, it is confirmed whether channel-direction collimator control and data acquisition corresponding to all views are completed.

Figure 34:
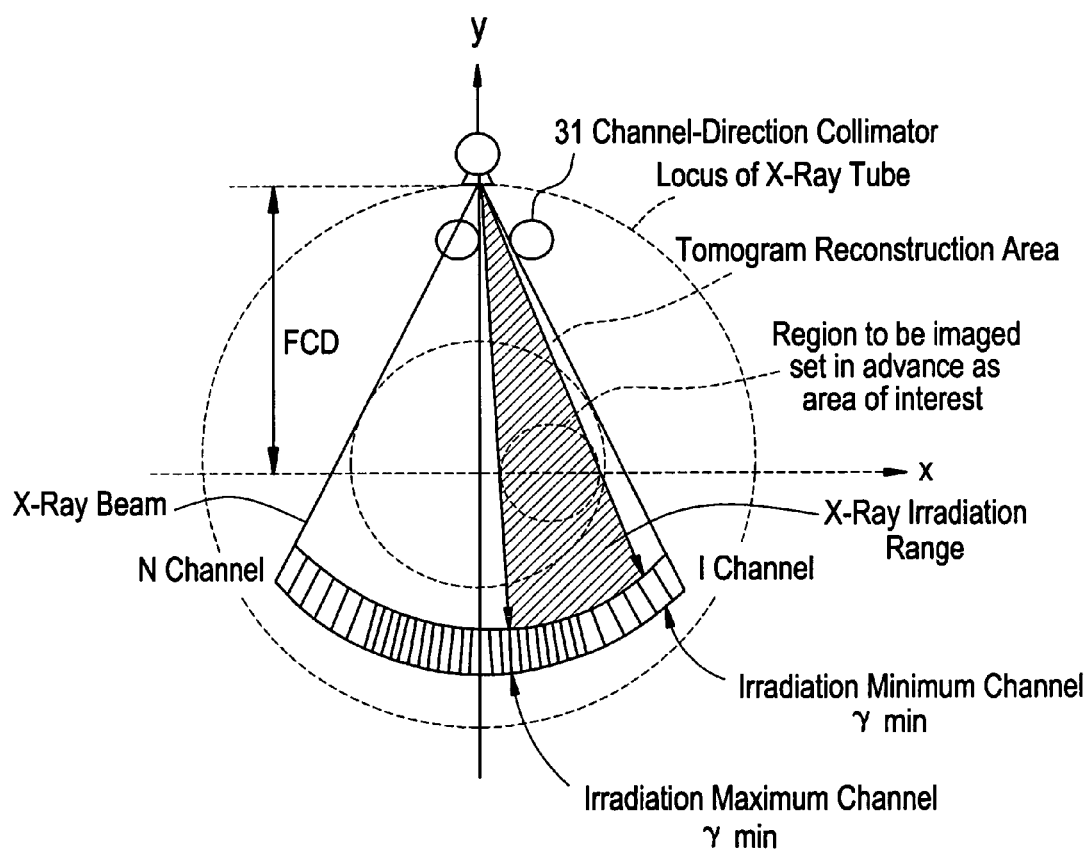
FIG. 34 is an explanatory view of an imaging area of interest and an irradiation channel range at the time of a view angle=0°.

Incidentally, the relationship among the minimum irradiation channel γmin and the maximum irradiation channel γmax, the data acquisition system comprising the X-ray tube 21, the multi-row X-ray detector 24 and the DAS 25, and the channel-direction collimator is shown in FIG. 34. As is understood from its relationship, the position (x, y) of an X-ray tube ball is expressed in x=FCD·sin θ, y=FCD·cos θ (where θ: view angle, and FCD (Focus Center Distance)).

Figure 35:
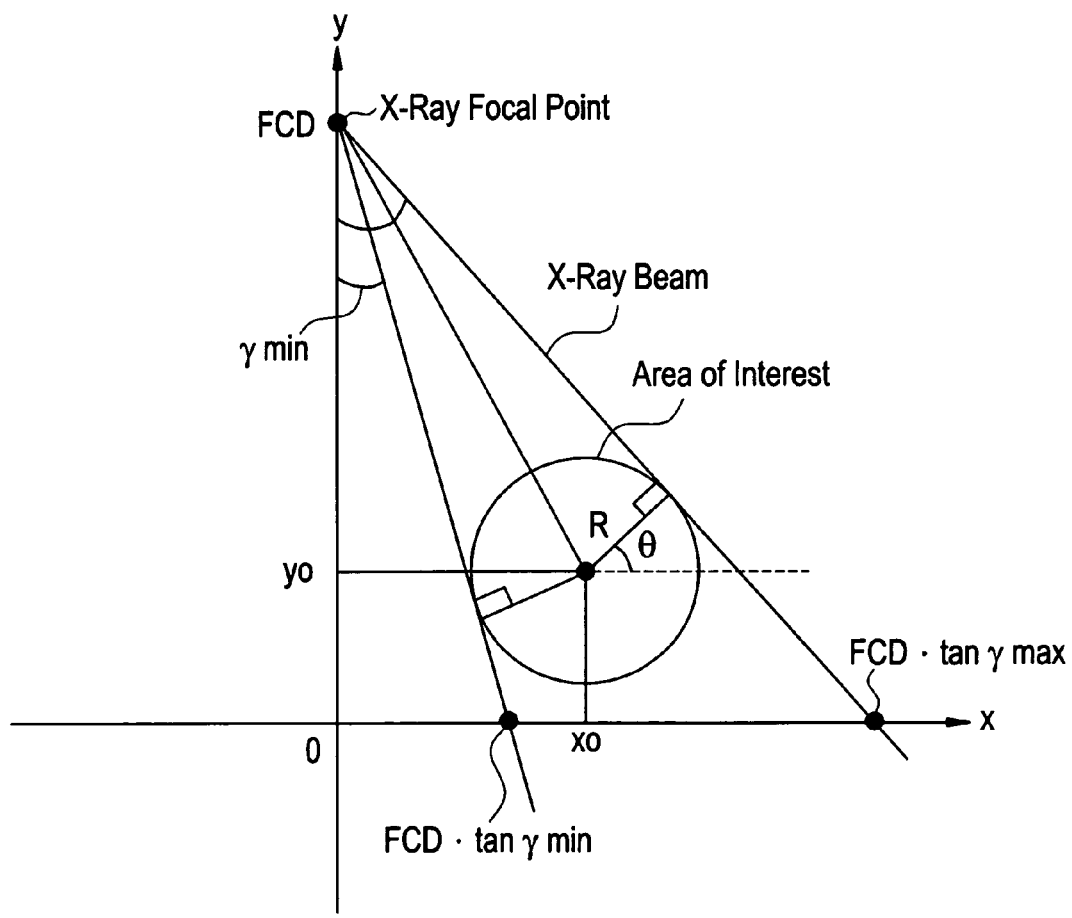
FIG. 35 is an explanatory view of an imaging area of interest, an irradiation minimum channel and an irradiation maximum channel at the time of a view angle=0°.

The relationship between an imaging area of interest at the time of a view angle=0°, and the minimum irradiation channel and maximum irradiation channel is as follows as described in FIG. 35.

When the position of, for example, a circular imaging area of interest is assumed to be (xo, yo), its radius is assumed to be R, its view angle is assumed to be 0°, i.e., an X-ray focal point is placed in (0, FCD), the above relationship is shown as expressed in the following equations (25), (26) and (27) (where FCD: Focus Center Distance). The following equations (28) and (29) are derived from the equations (25), (26) and (27). As expressed in the following equations (30) and (31), the maximum value of γ at this time becomes γmax and the minimum value of γ becomes γmin.

$$\begin{cases} y = \frac{1}{\tan\gamma} \cdot x + FCD \\ x = xo + R \cdot \sin\theta \\ y = yo + R \cdot \cos\theta \end{cases} \quad (25)(26)(27)$$

$$\tan\gamma = \frac{-x}{FCD - y} \quad (28)$$

$$y = \tan^{-1}\left(\frac{-x}{FCD - y}\right)$$

$$= \tan^{-1}\left(\frac{-xo - R \cdot \sin\theta}{FCD - yo - R \cdot \cos\theta}\right) \quad (29)$$

$$\gamma\max = \tan^{-1}\left(\frac{xo}{FCD - yo}\right) + \sin^{-1}\left(\frac{R}{\sqrt{(FCD - yo)^2 + xo^2}}\right) \quad (30)$$

$$\gamma\min = \tan^{-1}\left(\frac{xo}{FCD - yo}\right) + \sin^{-1}\left(\frac{R}{\sqrt{(FCD - yo)^2 + xo^2}}\right) \quad (31)$$

Figure 36:
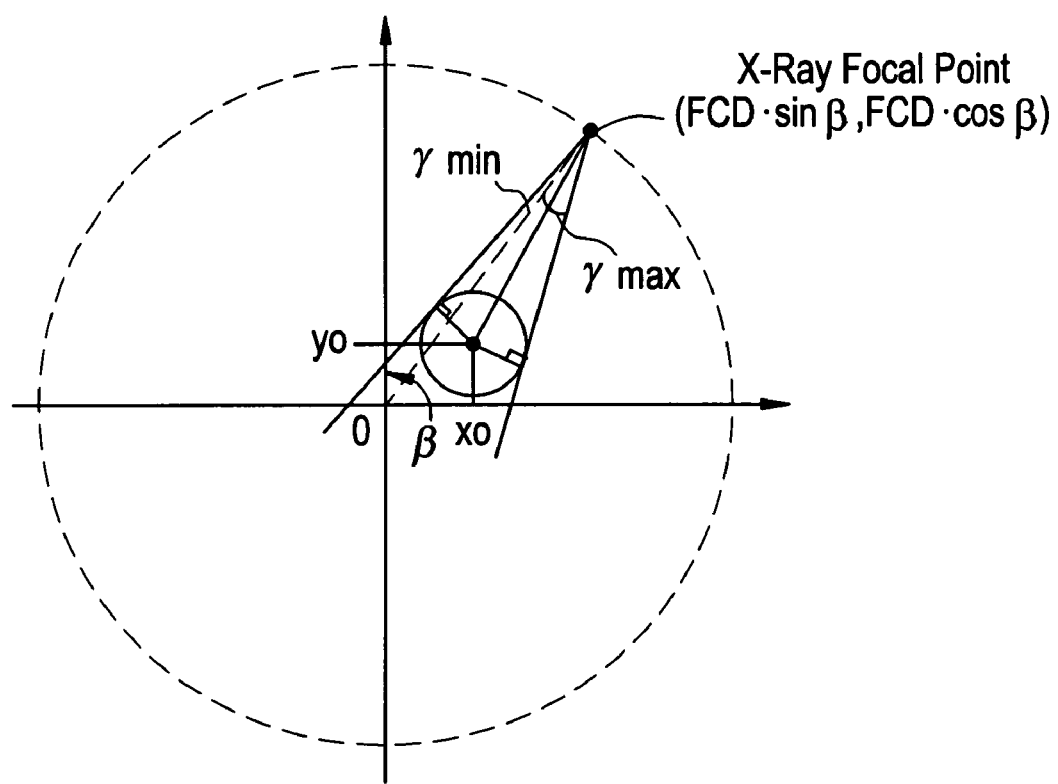
FIG. 36 is an explanatory view of an imaging area of interest, an irradiation minimum channel and an irradiation maximum channel at the time of a view angle=β.

The relationship between an imaging area of interest at the time of a view angle=β, and the minimum irradiation channel and maximum irradiation channel is as follows as described in FIG. 36.

When the position of, for example, a circular imaging area of interest is assumed to be (xo, yo), its radius is assumed to be R, its view angle is assumed to be 0°, that is, an X-ray focal point is placed in (FCD·sin β, FCD·cos β), the above relationship is shown as expressed in the following equations (32), (33) and (34) (where FCD: Focus Center Distance). The following equation (35) is derived from the equations (32), (33) and (34). From the following equations (36) and (37), the maximum value of γ at this time becomes γmax and the minimum value of γ becomes γmin, as expressed in the following equations (38) and (39).

$$\begin{cases} y = \frac{1}{\tan(\beta+\gamma)} \cdot (x - FCD \cdot \sin\beta) + FCD \cdot \cos\beta \\ x = xo + R \cdot \sin\theta \\ y = yo + R \cdot \cos\theta \end{cases} \quad (32)(33)(34)$$

$$\tan(\beta + \gamma) = \frac{FCD \cdot \sin\beta - x}{FCD \cdot \cos\beta - y} \quad (35)$$

$$y = \tan^{-1}\left(\frac{FCD \cdot \sin\beta - xo - R \cdot \sin\theta}{FCD \cdot \cos\beta - yo - R \cdot \cos\theta}\right) - \beta$$

$$xo' = xo \cdot \cos\beta - yo \cdot \sin\beta \quad (36)$$

$$yo' = xo \cdot \sin\beta + yo \cdot \cos\beta \quad (37)$$

$$\gamma\max = \tan^{-1}\left(\frac{xo'}{FCD - yo'}\right) + \sin^{-1}\left(\frac{R}{\sqrt{(FCD - yo')^2 + xo'^2}}\right) \quad (38)$$

$$\gamma\min = \tan^{-1}\left(\frac{xo'}{FCD - yo'}\right) + \sin^{-1}\left(\frac{R}{\sqrt{(FCD - yo')^2 + xo'^2}}\right) \quad (39)$$

Figure 37:
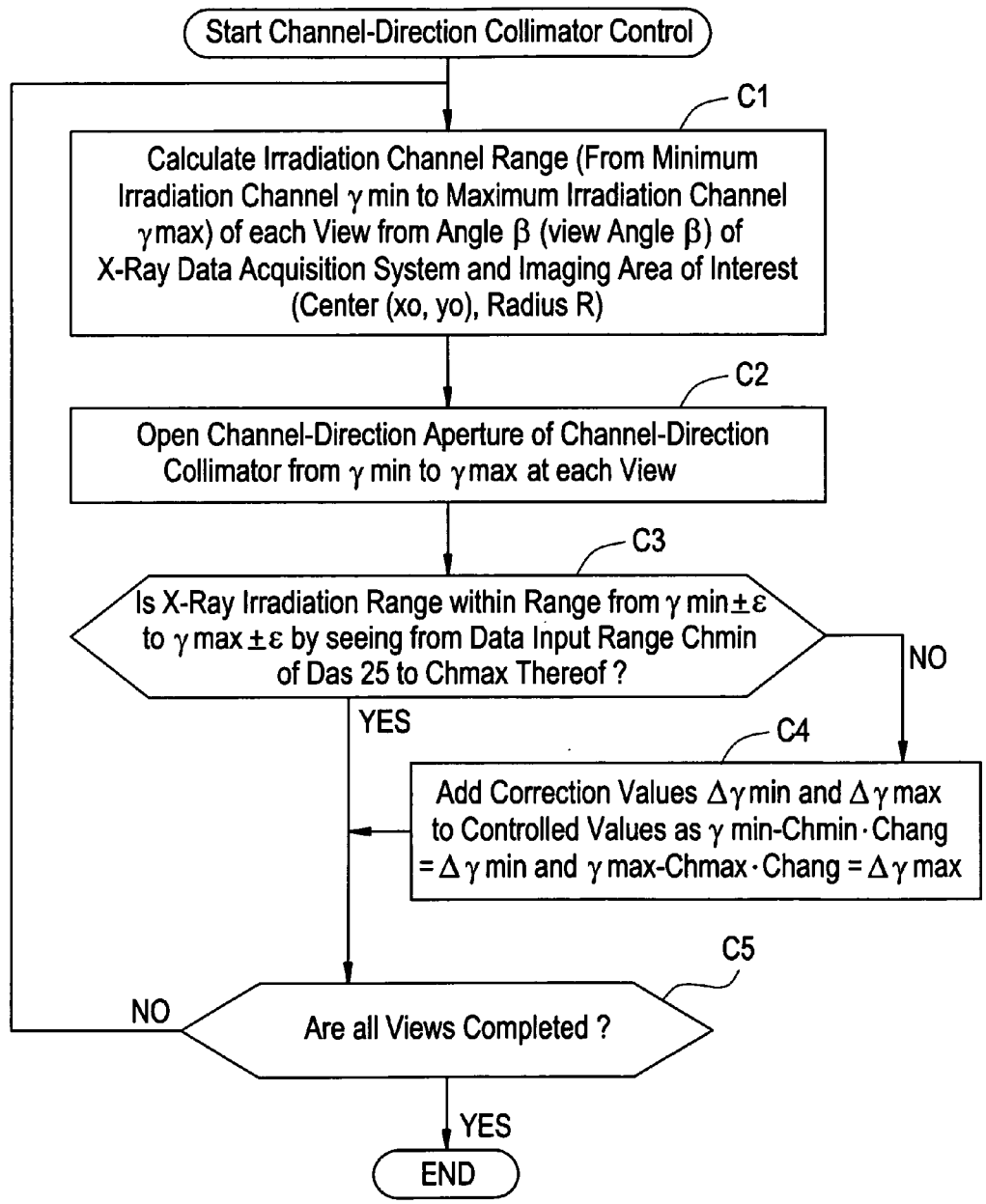
FIG. 37 is a diagram showing feedback control of the channel-direction collimator.

Feedback control of a channel-direction X-ray collimator is next shown in FIG. 37.

In Step C1, in a manner similar to Step C1 of FIG. 33, an angular range (from the minimum irradiation channel γmin to the maximum irradiation channel γmax) or a channel range on the multi-row X-ray detector 24 to radiate X rays is determined by calculation according to an angle β (view angle β) of an X-ray data acquisition system comprised of the X-ray tube 21, multi-row X-ray detector 24 and DAS 25, and the size and position of an imaging area of interest (e.g., a circular area of interest whose center is (xo, yo) and whose radius is R).

In Step C2, the channel-direction collimator (which may be an eccentric cylindrical collimator or a shielding plate-like collimator) is made open from the minimum irradiation channel γmin to the maximum irradiation channel γmax in a manner similar to Step C2 of FIG. 34.

In Step C3, the range of data irradiated with X rays is determined while data of the DAS25 is being viewed. Assuming that a range from Chmin to Chmax is a data input range irradiated with the X rays, it is confirmed whether it corresponds to the minimum irradiation channel γmin or the maximum irradiation channel γmax determined in Step C1.

If the data input range falls within a range of a minute error of ±ε, then no problem occurs. When, however, it exceeds this error range, the feedback control proceeds to Step C4.

In Step C4, correction amounts or values Δγmin and Δγmax are added to controlled amounts or values assuming that γmin−Chmin·Chang=Δγmin, γmax−Chmax·Chang=Δγmax. Thereafter, the feedback control proceeds to Step C5.

In Step C5, it is confirmed whether data acquisition corresponding to all views is completed. If it is not completed, then the feedback control is returned to Step C1, where the channel-direction collimator control and the data acquisition are performed continuously.

In this case, an elliptic approximation is made from the area of a profile and the width thereof in a channel direction. As shown in FIG. 32, projection data Sil and Sir added to the left and right sides of a portion or region to be imaged are recognized or known by masked X-ray data in respective directions at an ith slice from the relationship of position between a profile subjected to an elliptic approximation and an area to be imaged. By adding Sil and Sir to the right and left of projection data and image-reconstructing the same, a tomographic image whose quality is better can be obtained.

As described above, the present embodiment is provided with the channel-direction collimator 31 which shields X rays radiated into a subject to thereby adjust the range of irradiation of the X rays as viewed in a channel direction. Upon scanning the subject, the control controller 29 controls an aperture position of the channel-direction collimator 31 in such a manner that the X rays from the X-ray tube 21 are irradiated in association with the area of interest of the subject inputted to the input device 2 by an operator. The central processing unit 3 allows the channel-direction collimator 31 to approximate lacked data about areas around the area of interest to each other and correct the same, based on X-ray detector data about the area of interest acquired by the multi-row X-ray detector 24. Thereafter, a tomographic image of the subject is image-reconstructed based on the approximated X-ray detector data. It is therefore possible to realize low exposure to radiation.

Embodiment 3

An embodiment 3 shows an example in which a beam forming X-ray filter 32 is used. The present embodiment is similar to the embodiment 1 except that the operation of an X-ray CT apparatus 100 is different from the embodiment 1. Therefore, dual portions will not be explained.

Although the embodiment 2 has been described using the channel-direction X-ray collimator 31, similar effects can be brought about even when the beam forming X-ray filter 32 is used as shown in FIG. 38.

Figure 38A:
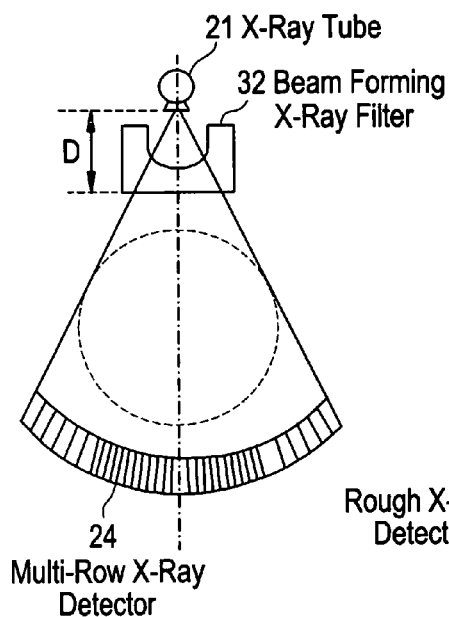
FIG. 38(a) is a diagram showing a normal position of a beam forming X-ray filter 32.

FIG. 38(a) shows the manner in which the normal position of the channel-direction X-ray collimator 31, i.e., the amount of traveling thereof in a channel direction is 0.

Figure 38B:
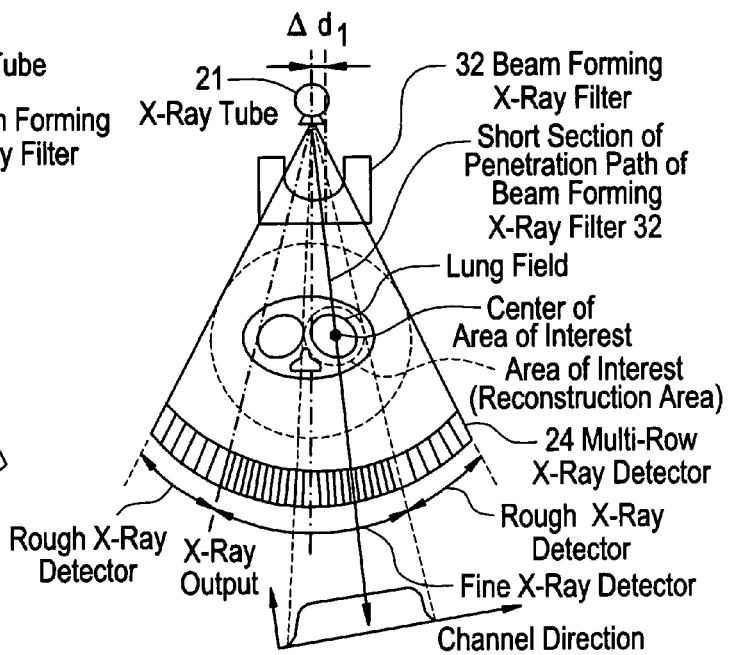
FIG. 38(b) is a diagram showing position control (part 1) on the beam forming X-ray filter 32.
Figure 38C:
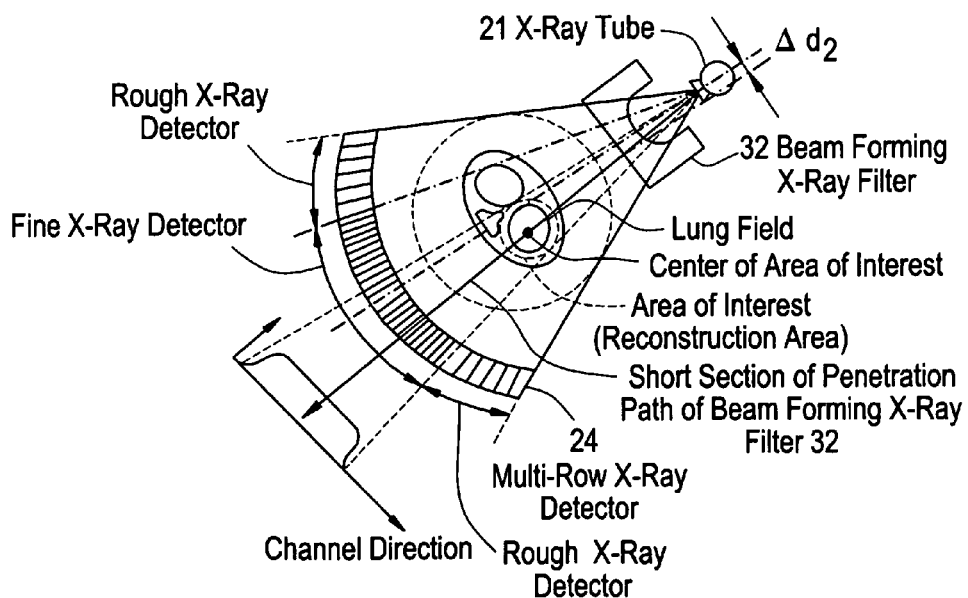
FIG. 38(c) is a diagram showing position control (part 2) on the beam forming X-ray filter 32.

FIGS. 38(b) and 38(c) respectively show where the amount of traveling of the beam forming X-ray filter 32 is taken as $d_1$ and $d_2$. In this case, a straight line that connects the center of an area of interest and an X-ray focal point may be controlled so as to be superimposed on such a straight line that an X-ray penetration path of the beam forming X-ray filter 32 becomes shortest.

In order to allow them to overlap each other, the following equation (40) derived from the equations (38) and (39) is used.

$$\gamma mean = (\gamma max + \gamma min)/2 \quad (40)$$

Assuming that the distance between the X-ray focal point and the beam forming X-ray filter 32 is D as shown in FIG. 38(a), it is expressed in an equation (41) shown below:

$$d_i = D \cdot \tan(\gamma mean) \quad (41)$$

where $d_i = d_1$ or $d_2$

According to the above X-ray CT apparatus 100, such an X-ray CT apparatus as to be capable of obtaining high resolution even by a helical scan and a conventional scan (axial scan) by using the X-ray CT apparatus of the present invention can be realized.

An X-ray CT apparatus can be realized which is capable of obtaining high resolution when only a limited area of interest is photographed and image-reconstructed.

An X-ray CT apparatus can be realized which is capable of obtaining high resolution at low exposure to radiation when only a limited area of interest is irradiated with X rays and photographed.

Described specifically, the X-ray CT apparatus 100 according to the present embodiment is provided with the beam forming X-ray filter 32 which adjusts an irradiation distribution of X rays in a channel direction. The control controller 29 controls the position of the X-ray filter 32 in such a manner that upon photographing a subject, the X rays from the X-ray tube 21 are radiated in association with an area of interest of the subject inputted to the input device 2 by an operator. Therefore, low exposure to radiation can be realized.

Incidentally, although the multi-row X-ray detector is used in the present embodiment, similar effects can be brought about even in the case of an X-ray CT apparatus using a single-row X-ray detector.

Although the three-dimensional image reconstruction method is used in the image reconstruction in the present embodiment, a three-dimensional image reconstruction method based on a Feldkamp method known to date or another three-dimensional image reconstruction method or a two-dimensional image reconstruction method may be used, and similar effects can be brought about even in this case.

Although the present embodiment makes use of the helical scan or the conventional scan (axial scan), similar effects can be brought about even in the case of a cine scan.

Many widely different embodiments of the invention may be configured without departing from the spirit and the scope of the present invention. It should be understood that the present invention is not limited to the specific embodiments described in the specification, except as defined in the appended claims.

The invention claimed is:

1. An X-ray CT apparatus comprising:
an X-ray data acquisition device comprising an X-ray generator and an X-ray detector positioned opposite the X-ray generator such that the X-ray generator and the X-ray detector are rotated about a center of rotation placed between the X-ray generator and the X-ray detector, the X-ray data acquisition device configured to acquire projection data of X-rays transmitted through a subject disposed between the X-ray generator and the X-ray detector, the X-ray data acquisition device is further configured such that a second detector channel width, $d_2$, located at each peripheral portion of the X-ray detector as viewed in a channel direction becomes $d_1 < d_2$ with respect to a first detector channel width, $d_1$, located at a central portion of the X-ray detector as viewed in the channel direction or such that a plurality of detector widths, $(d_1, d_2, \ldots d_i, \ldots d_{n-1}, d_n)$, provided from the central portion of the X-ray detector as viewed in the channel direction to the peripheral portion of the X-ray detector, are sized such that $d_1 \leq d_2 \leq \ldots \leq d_i \leq \ldots \leq d_{n-1} \leq d_n$, the X-ray data acquisition device further comprising a plurality of data acquisition sampling periods at which data acquisition is performed, the plurality of data acquisition sampling periods differing according to channel positions;
an image reconstructing device configured to image-reconstruct the projection data acquired from the X-ray data acquisition device;
a display device configured to display an image-reconstructed image generated by the image reconstructing device; and
a control device configured to control an X-ray irradiation area in a row direction such that the X-ray irradiation area differs according to positions in the channel direction.

2. An X-ray CT apparatus comprising:
an X-ray data acquisition device comprising an X-ray generator and an X-ray detector positioned opposite the X-ray generator such that the X-ray generator and the X-ray detector are rotated about a center of rotation placed between the X-ray generator and the X-ray detector, the X-ray data acquisition device configured to acquire projection data of X-rays transmitted through a subject disposed between the X-ray generator and the X-ray detector, the X-ray data acquisition device comprising a plurality of data acquisition ranges $1_1 \geq 1_2 \geq \ldots \geq 1_i \geq \ldots \geq 1_{n-1} \geq 1_n$ arranged such that a first data acquisition range, $1_1$, is wider in a channel direction of the X-ray detector than an $n^{th}$ data acquisition range, $1_n$, the X-ray data acquisition device further configured such that the plurality of data acquisition ranges are switchable every data acquisition, the X-ray data acquisition device further comprising a plurality of data acquisition sampling periods at which data acquisition is performed, the plurality of data acquisition sampling periods differing according to channel positions;
an image reconstructing device configured to image-reconstruct the projection data acquired from the X-ray data acquisition device;
a display device configured to display an image-reconstructed image generated by the image reconstructing device; and
a control device configured to control an X-ray irradiation area in a row direction such that the X-ray irradiation area differs according to positions in the channel direction.

3. The X-ray CT apparatus according to claim 1, wherein the X-ray data acquisition device is further configured to perform data acquisition at the central portion of the X-ray detector as viewed in the channel direction, the central portion having a narrower detector channel width than a detector channel width at the peripheral portion of the X-ray detector.

4. The X-ray CT apparatus according to claim 1, wherein the X-ray data acquisition device comprises a plurality of channels at which data acquisition is performed.

5. The X-ray CT apparatus according to claim 1, wherein the X-ray data acquisition device comprises a plurality of channels at which data acquisition is performed, and a plurality of views.

6. The X-ray CT apparatus according to claim 1, wherein the X-ray data acquisition device comprises a plurality of rows at which data acquisition is performed such that a number of rows differs according to each channel position.

7. The X-ray CT apparatus according to claim 1, wherein the control device is configured to control the X-ray irradiation area in such a manner that X-rays are radiated only into some of the central portion of the X-ray detector as viewed in the channel direction, the central portion of the X-ray detector having a narrower detector channel width than a detector channel width at the peripheral portion of the X-ray detector.

8. The X-ray CT apparatus according to claim 1, wherein the control device comprises a channel-direction collimator.

9. The X-ray CT apparatus according to claim 2, wherein the X-ray data acquisition device is configured to perform data acquisition at the central portion of the X-ray detector as viewed in the channel direction, the central portion having a narrower detector channel width than a detector channel width at the peripheral portion of the X-ray detector.

10. The X-ray CT apparatus according to claim 2, wherein the X-ray data acquisition device comprises a plurality of channels at which data acquisition is performed.

11. The X-ray CT apparatus according to claim 2, wherein the X-ray data acquisition device comprises a plurality of channels at which data acquisition is performed, and a plurality of views.

12. The X-ray CT apparatus according to claim 2, wherein the X-ray data acquisition device comprises a plurality of rows at which data acquisition is performed such that a number of rows differs according to each channel position.

13. The X-ray CT apparatus according to claim 2, wherein said the control device is configured to control an X-ray irradiation area in such a manner that X-rays are radiated only into some of the central portion of the X-ray detector as viewed in the channel direction, the central portion of the X-ray detector having a narrower detector channel width than a detector channel width at the peripheral portion of the X-ray detector.

14. The X-ray CT apparatus according to claim 2, wherein the control device comprises a channel-direction collimator.

15. The X-ray CT apparatus according to claim 1, wherein the control device comprises a beam forming X-ray filter.

16. The X-ray CT apparatus according to claim 2, wherein the control device comprises a beam forming X-ray filter.

* * * * *